US011890386B2

(12) United States Patent
Ruan et al.

(10) Patent No.: US 11,890,386 B2
(45) Date of Patent: Feb. 6, 2024

(54) DISINFECTING MATERIALS WITH INTENSE PULSED LIGHT AND CATALYTIC MICROWAVE-ASSISTED DECONTAMINATION

(71) Applicant: REGENTS OF THE UNIVERSITY OF MINNESOTA, Minneapolis, MN (US)

(72) Inventors: Rongsheng Ruan, Arden Hills, MN (US); Yanling Cheng, St. Paul, MN (US); Nan Zhou, St. Paul, MN (US); Dongjie Chen, St. Paul, MN (US); Peng Peng, Lauderdale, MN (US); Yunpu Wang, St. Paul, MN (US); Renchuan Zhang, St. Paul, MN (US); Charles Schiappacasse, Maplewood, MN (US); Ling Chen, Roseville, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 624 days.

(21) Appl. No.: 16/818,795

(22) Filed: Mar. 13, 2020

(65) Prior Publication Data
US 2020/0289681 A1    Sep. 17, 2020

Related U.S. Application Data

(60) Provisional application No. 62/819,040, filed on Mar. 15, 2019, provisional application No. 62/883,557, (Continued)

(51) Int. Cl.
*A61L 2/00* (2006.01)
*B01J 35/00* (2006.01)
(Continued)

(52) U.S. Cl.
CPC ............ *A61L 2/0047* (2013.01); *A23L 3/005* (2013.01); *A61L 2/0076* (2013.01);
(Continued)

(58) Field of Classification Search
CPC .. A61L 2/0047; A61L 2202/21; B01J 35/004; B01J 21/063; A23L 3/005
(Continued)

(56) References Cited

U.S. PATENT DOCUMENTS

| 2008/0130399 | A1* | 6/2008 | Littman | ................. | B01F 23/60 |
| | | | | | 366/132 |
| 2012/0288589 | A1* | 11/2012 | Chalupa | ................. | A23N 15/06 |
| | | | | | 426/248 |
| 2016/0143116 | A1* | 5/2016 | Chen | ..................... | A23B 7/015 |
| | | | | | 315/210 |

FOREIGN PATENT DOCUMENTS

JP          2004065239 A  *  3/2004  .......... A61L 2/0047

OTHER PUBLICATIONS

English Translation of The Description Section for JP 2004065239 A.*

(Continued)

*Primary Examiner* — Monzer R Chorbaji
(74) *Attorney, Agent, or Firm* — Fish & Richardson P.C.

(57) ABSTRACT

Disinfecting particulate material includes combining the particulate material with a photocatalyst to yield a mixture, irradiating the mixture for a length of time with pulses from a light source having broadband emission spectrum between 190 nm-1100 nm to yield an irradiated mixture, and separating the photocatalyst from the disinfected mixture to yield the disinfected particulate matter. Irradiating the mixture inactivates microorganisms in the mixture to yield a disinfected mixture. A system for disinfecting particulate material includes a pulsed light source having a broadband emission spectrum in a range between about 190 nm and about 1100
(Continued)

nm, a chamber defining a cavity optically coupled to the pulsed light source, a humidifier, a fan, and one or more sensors. The chamber includes a conveyor configured to accept the particulate material and arranged such that the pulses emitted by the pulsed light source irradiate the particulate material on the conveyor.

24 Claims, 12 Drawing Sheets

Related U.S. Application Data filed on Aug. 6, 2019, provisional application No. 62/883,915, filed on Aug. 7, 2019.

(51) Int. Cl.
  *B01J 21/06* (2006.01)
  *A23L 3/005* (2006.01)
(52) U.S. Cl.
  CPC .......... *B01J 21/063* (2013.01); *B01J 35/004* (2013.01); *A61L 2202/21* (2013.01)
(58) Field of Classification Search
  USPC .......................................................... 422/24
  See application file for complete search history.

(56) References Cited

OTHER PUBLICATIONS

Buchholz et al., "Reduction of *Salmonella* on alfalfa wheat grains using peroxyacetic acid and a commercial seed washer is as effective as treatment with 20,000 ppm of Ca(OCI)2". Lett. Appl. Microbiology, Aug. 2010, 51:462-468.

CDC.gov [online], "Multistate Outbreak of Shiga toxin-producing *Escherichia coli* Infections Linked to Flour (Final Update)," Sep. 29, 2016, retrieved on Sep. 4, 2020, retrieved from Url<https://www.cdc.gov/ecoli/2016/o121-06-16/index.html>, 3 pages.

CDC.gov [online], "Outbreak of *E. coli* Infections Linked to Flour," Jul. 11, 2019, retrieved on Sep. 4, 2020, retrieved from URL <https://www.cdc.gov/ecoli/2019/flour-05-19/index.html>, 4 pages.

Chen et al., "Effects of intense pulsed light on Cronobacter sakazakii and *Salmonella* surrogate Enterococcus faecium incoulated in different powdered foods," Food Chemistry, Oct. 2019, 296:23-28.

Chen et al., "Effects of intense pulsed light on Cronobacter sakazakii inoculated in non-fat dry milk," J. Food Engineering, Dec. 2018, 238:178-187.

Chen et al., "Evaluation of Cronobacter sakazakii inactivation and physicochemical property changes of non-fat dry milk powder by cold atmospheric plasma," Food Chemistry, Aug. 2019, 290:270-276.

Datta et al., "Microwave and Radio Frequency Processing," J. Food Science, Nov. 2000, 65(s8):32-41.

Dev et al., "Dielectric properties of egg components and microwave heating for in-shell pasteurization of eggs," J. Food Engineering, May 2008, 86(2):207-214.

Erkkila et al., "Cereal fiber and whole-grain intake are associated with reduced progression of coronary artery atherosclerosis in postmenopausal women with coronary artery disease," Am. Heart Journal, Jul. 2005, 150(1):94-101.

Espino-Estevez et al., "Enhancement of stability and photoactivity of TiO2 coatings on annular glass reactors to remove emerging pollutants from waters," Chem. Eng. Journal, Nov. 2015, 279(1):488-497.

Gunasekaran et al., "Effect of experimental parameters on temperature distribution during continuous and pulsed microwave heating," J. Food Engineering, Feb. 2007, 78(4):1452-1456.

Healthycanadians.gc.ca [online], "Certain bulk and prepackaged raw shelled walnuts may contain *E. coli* O157:H7 bacteria," Apr. 3, 2011, retrieved on Sep. 4, 2020, retrieved from URL <https://www.healthycanadians.gc.ca/recall-alert-rappel-avis/inspection/2011/33573r-eng.php>, 2 pages.

Horikoshi et al., "Environmental Remediation by an Integrated Microwave/UV Illumination Method. V. Thermal and Nonthermal Effects of Microwave Radiation on the Photocatalyst and on the Photodegradation of Rhodamine-B under UV/Vis Radiation," Environ. Sci. Technology, Nov. 2003, 37(24):5813-5822.

Horikoshi et al., "Hydroxyl radicals in microwave photocatalysis. Enhanced formation of OH radicals probed by ESR techniques in microwave-assisted photocatalysis in aqueous TiO2 dispersions," Chem. Phys. Letters, Jul. 2003, 376(3-4):475-480.

Horikoshi et al., "Influence of lattice distortion and oxygen vacancies on the UV-driven/microwave-assisted TiO2 photocatalysis," J. Photoch. Photobio. A: Chemistry, Aug. 2013, 265:20-28.

Kozempel et al., "Inactivation of microorganisms with microwaves at reduced temperatures," J. Food Protection, May 1998, 61(5):582-585.

Lau et al., "Pasteurization of pickled asparagus using 915 MHz microwaves," J. Food Engineering, 2002, 51:283-290.

Liu et al., "Synergistic biological effect of microwave and ultraviolet in sterilization," Chinca Acdemic Journal Electronic Publishing House: Food Science and Technology, 2007, 12:140-142, (with English abstract).

Magan et al., "Post-harvest fungal ecology: impact of fungal growth and mycotoxin accumulation in stored grain," Eur. J. Plant Pathology, Sep. 2003, 109:723-730.

Manickavasagan et al., "Non-Uniformity of Surface Temperatures of Grain after Microwave Treatment in an Industrial Microwave Dryer," Drying Technology, Dec. 2006, 24(12):1559-1567.

McIntosh et al., "Whole-grain rye and wheat foods and markers of bowel health in overweight middle-aged men," Am. J. Clin. Nutrition, Apr. 2003, 77(4):967-974.

Muller et al., "Cluster of *Salmonella enteritidis* in Sweden 2005-2006 -suspected source: almonds," Eurosurveillance, Jun. 2007, 12(6):153-155.

Pereira et al., "Effect of whole grains on insulin sensitivity in overweight hyperinsulinemic adults," Am. J. Clin. Nutrition, May 2002, 75(5):848-855.

Richard, "Some major mycotoxins and their mycotoxicoses—an overview," Int. J. Food Microbiology, Oct. 2007, 119(1-2):3-10.

Scallan et al., "Foodborne illness acquired in the United States-major pathogens," Emerg. Infect. Diseases, Jan. 2011, 17(1):7-15.

Shenga et al., "Effect of pasteurization of shell egg on its quality characteristics under ambient storage," J. Food Sci. Technology, Aug. 2010, 47(4):420-425.

Stadler et al., "Automated Library Generation Using Sequential Microwave-Assisted Chemistry. Application toward the Biginelli Multicomponent Condensation," J. Comb. Chemistry, Nov. 2001, 3(6):624-630.

Strohmeier et al., "Rapid Parallel Synthesis of Polymer-Bound Enones Utilizing Microwave-Assisted Solid-Phase Chemistry," J. Comb. Chemistry, Mar. 2002, 4(2):154-161.

The Microbiological Safety of Low Water Activity Foods and Spices: Food Microbiology and Food Safety, Gurtler et al. (eds.), 2014, Part IV(2):367-386.

U.S. Department of Health and Human Services, "Healthy People 2010: Understanding and Improving Health," 2nd ed., Nov. 2000, 76 pages.

Vadivambal et al., "Wheat disinfestation using microwave energy," J. Stored Prod. Research, Jan. 2007, 43(4):508-514.

Wan et al., "Highly effective methane conversion to aromatic hydrocarbons by means of microwave and rf-induced catalysis," Res. Chem. Intermediates, 2000, 26(6):599-619.

Wiertzema et al., "Evaluation of Methods for Inoculating Dry Powder Foods with *Salmonella enterica*, Enterococcus faecium, or Cronobacter sakazakii," J. Food Protection, May 2019, 82(6):1082-1088.

Aguilera et al., "Caking phenomena in amorphous food powders," Trends Food Sci. Technol., May 1995, 6(5):149-155.

Aguirre et al., "Estimation of the growth kinetic parameters of Bacillus cereus spores as affected by pulsed light treatment," Int. J. Food Microbiol., Jun. 2015, 202:20-26.

(56) References Cited

OTHER PUBLICATIONS

Akbas et al., "Effect of gaseous ozone on microbial inactivation and sensory of flaked red peppers," Int. J. Food Sci. Technol., Aug. 2008, 43(9):1657-1662.

Annous et al., "Influence of Growth Medium on Thermal Resistance of Pediococcus sp. NRRL B-2354 (Formerly Micrococcus freudenreichii) in Liquid Foods," J. Food Prot., May 1998, 61(5):578-581.

Archer et al., "Heat Resistance of *Salmonella* weltevreden in Low-Moisture Environments," J. Food Prot., Aug. 1998, 61(8):969-973.

Bari et al., "Effectiveness of sanitizers, dry heat, hot water, and gas catalytic infrared heat treatments to inactivate *Salmonella* on almonds," Foodborne Pathog. Dis., Oct. 2009, 6(8):953-958.

Blazquez et al., "Ultraviolet (UV-C) inactivation of Enterococcus faecium, *Salmonella choleraesuis* and *Salmonella typhimurium* in porcine plasma," PLoS One, Apr. 2017, 12(4):e0175289, 11 pages.

Ceylan et al., "Evaluating Pediococcus acidilactici and Enterococcus faecium NRRL B-2354 as Thermal Surrogate Microorganisms for *Salmonella* for In-Plant Validation Studies of Low-Moisture Pet Food Products," J. Food Prot., May 2015, 78(5):934-939.

Cheigh et al., "Comparison of intense pulsed light- and ultraviolet (UVC)-induced cell damage in Listeria monocytogenes and *Escherichia coli* O157:H7," Food Control, Jun. 2012, 25(2):654-659.

Chen et al., "Catalytic intense pulse light inactivation of Cronobacter sakazakii and other pathogens in non-fat dry milk and wheat flour," Food Chem., Dec. 2020, 332:127420, 9 pages.

Chen et al., "Deoxynivalenol Decontamination in Raw and Germinating Barley Treated by Plasma-Activated Water and Intense Pulsed Light," Food Bioprocess. Technol., Nov. 2018, 12:246-254.

Chung et al., "Inactivation of *Staphylococcus aureus* and *Escherichia coli* under various light sources on photocatalytic titanium dioxide thin film," Surf. Coat. Technol., Jan. 2009, 203(8):1081-1085.

Cirkva and Relich, "Microwave Photochemistry and Photocatalysis. Part 1: Principles and Overview," Curr. Org. Chem., Mar. 2011, 15(2):248-264.

Ehling-Schulz et al., "Bacillus cereus in Milk and Dairy Production," Rapid Detection, Characterization, and Enumeration of Foodborne Pathogens, American Society of Microbiology, Apr. 2011, Chapter 19, 15 pages.

Elmnasser et al., "Bacterial Inactivation Using Pulsed Light," Acta Alimentaria, Sep. 2007, 36(3):401-408.

Feng et al., "Application of immobilized TiO2 photocatalysis to improve the inactivation of Heterosigma akashiwo in ballast water by intense pulsed light," Chemosphere, Apr. 2015, 125:102-107.

Fine et al., "Efficiency of Pulsed UV Light for Microbial Decontamination of Food Powders," J. Food Prot., Apr. 2004, 67(4):787-792.

Food and Agriculture Organization and World Health Organization, "Enterobacter sakazakii and other microorganisms in powdered infant formula: meeting report," MRA series 6, 2004, World Health Organization, Geneva, 80 pages.

Food and Agriculture Organization and World Health Organization, "Enterobacter sakazakii and *Salmonella* in powdered infant formula: meeting report," MRA series 10, 2006, World Health Organization, Geneva, 121 pages.

Forghani et al., "*Salmonella* and Enterohemorrhagic *Escherichia coli* Serogroups O45, O121, O145 in Wheat Flour: Effects of Long-Term Storage and Thermal Treatments," Front. Microbiol., Feb. 2019, 10:323, 12 pages.

Foster et al., "Photocatalytic disinfection using titanium dioxide: spectrum and mechanism of antimicrobial activity," Appl. Microbiol. Biotechnol., Apr. 2011, 90(6):1847-1868.

Freita-Silva et al., "Potential of Electron Beams to Control Mycotoxigenic Fungi in Food," Food Eng. Rev., Sep. 2014, 7:160-170.

Gökmen et al., "Presence of Enterobacter sakazakii in milk powder, whey powder and white cheese produced in Konya," Kafkas Univ. Vet. Fak. Derg, Jan. 2010, 16(Suppl A):S163-S166.

Granum et al., "Analysis of enterotoxin production by Bacillus cereus from dairy products, food poisoning incidents and non-gastrointestinal infections," Int. J. Food Microbiol., Feb. 1993, 17(4):269-279.

Greenspan, "Humidity Fixed Points of Binary Saturated Aqueous Solutions," J. Res. Natl. Bur. Stand. A. Phys. Chem., Jan.-Feb. 1977, 81A(1):89-96.

Gurol et al., "Low Temperature Plasma for decontamination of *E. coli* in milk," Int. J. Food Microbiol., Jun. 2012, 157(1):1-5.

Kandhai et al., "Occurrence of Enterobacter sakazakii in food production environments and households," The Lancet, Jan. 2004, 363(9402):39-40.

Kim et al., "Thermal resistance and inactivation of Enterobacter sakazakii isolates during rehydration of powdered infant formula," J. Microbiol. Biotechnol., Feb. 2007, 17(2):364-368.

Koseki et al., "Effect of Nitrogen Gas Packaging on the Quality and Microbial Growth of Fresh-Cut Vegetables under Low Temperatures," J. Food Prot., Feb. 2002, 65(2):326-332.

Kowalska et al., "Silver-modified titania with enhanced photocatalytic and antimicrobial properties under UV and visible light irradiation," Catalysis Today, Sep. 2015, 252:136-142.

Krishnamurthy, "Decontamination of milk and water by pulsed UV-light and infrared heating," Thesis for the degree of Doctor of Philosophy, The Pennsylvania State Univ., Dept. of Agricultural and Biological Engineering, Aug. 2006, 244 pages.

Larsen et al., "Effect of Oxygen Transmission Rate of the Packages, Light, and Storage Temperature on the Oxidative Stability of Extruded Oat Packaged in Nitrogen Atmosphere," J. Food Sci., Jul. 2006, 68(3):1100-1108.

Levy et al., "Relevant factors affecting microbial surface decontamination by pulsed light," Int. J. Food Microbiol., Jan. 2012, 152(3):168-174.

Liu et al., "Microbial validation of radio frequency pasteurization of wheat flour by inoculated pack studies," J. Food Eng., Jan. 2018, 217:68-74.

Luksiene et al., "Advanced high-power pulsed light device to decontaminate food from pathogens: effects on *Salmonella typhimurium* viability in vitro," J. Appl. Microbiol., Nov. 2007, 103(5):1545-1552.

Mai-Prochnow et al., "Gram positive and Gram negative bacteria differ in their sensitivity to cold plasma," Sci. Rep., Dec. 2016, 6:38610, 11 pages.

Mancebo-Campos et al., "Kinetic study for the development of an accelerated oxidative stability test to estimate virgin olive oil potential shelf life," Eur. J. Lipid Sci. Technol., Oct. 2008, 110(10):969-976.

Markowska-Szczupak et al., "The application of titanium dioxide for deactivation of bioparticulates: An overview," Catalysis Today, Jul. 2011, 169(1):249-257.

Moeller et al., "Roles of small, acid-soluble spore proteins and core water content in survival of Bacillus subtilis spores exposed to environmental solar UV radiation," Appl. Environ. Microbiol., Aug. 2009, 75(16):5202-5208.

Mukisa et al., "Gamma irradiation of sorghum flour: Effects on microbial inactivation, amylase activity, fermentability, viscosity and starch granule structure," Radiation Phys. Chem., Mar. 2012, 81(3):345-351.

Nicroescu et al., "Pulsed light inactivation of Bacillus subtilis vegetative cells in suspensions and spices," Food Control, May 2013, 31(1):151-157.

Oms-Oliu et al., "Pulsed Light Treatments for Food Preservation. A Review," Food Bioprocess. Technol., Oct. 2008, 3:13-23.

Pina-Perez et al., "Cocoa powder as a natural ingredient revealing an enhancing effect to inactivate Cronobacter sakazakii cells treated by Pulsed Electric Fields in infant milk formula," Food Control, Jul. 2013, 31(1):87-92.

Podolak et al., "Sources and Risk Factors for Contamination, Survival, Persistence, and Heat Resistance of *Salmonella* in Low-Moisture Foods," J. Food Prot., Oct. 2010, 73(10):1919-1936.

Qu et al., "Effects of microwave heating of wheat on its functional properties and accelerated storage," Journal of Food Science and Technology, Sep. 2017, 54:3699-3706.

(56) References Cited

OTHER PUBLICATIONS

Reyes et al., "Prevalence of Bacillus cereus in dried milk products used by Chilean School Feeding Program," Food Microbiol., Feb. 2007, 24(1):1-6.

Ringus et al., "Pulsed Light inactivation of Listeria innocua on food packaging materials of different surface roughness and reflectivity," J. Food Eng., Feb. 2013, 114(3):331-337.

Roberts et al., "Virus inactivation by high intensity broad spectrum pulsed light," J. Virol. Methods, Jun. 2003, 110(1):61-65.

Rose et al., "Enhanced Lipid Stability in Whole Wheat Flour by Lipase Inactivation and Antioxidant Retention," Cereal Chem., Mar. 2008, 85(2):218-223.

Rowan et al., "Pulsed-light inactivation of food-related microorganisms," Appl. Environ. Microbiol., Mar. 1999, 65(3):1312-1315.

Ryu et al., "Effects of Selected Process Parameters on Expansion and Mechanical Properties of Wheat Flour and Whole Cornmeal Extrudates," Starch, Apr. 2001, 53(3-4):147-154.

Setlow, "Resistance of spores of Bacillus species to ultraviolet light," Environ. Mol. Mutagen., Feb. 2001, 38(2-3):97-104.

Sharma et al., "Inactivation of *Escherichia coli* O157:H7 on inoculated alfalfa seeds with pulsed ultraviolet light and response surface modeling," J. Food Sci., Jul. 2006, 68:1448-1453.

Slieman et al., "Artificial and Solar UV Radiation Induces Strand Breaks and Cyclobutane Pyrimidine Dimers in Bacillus subtilis Spore DNA," Appl. Environ. Microbiol., Jan. 2000, 66(1):199-205.

Sperber, "Role of Microbiological Guidelines in the Production and Commercial Use of Milled Cereal Grains: A Practical Approach for the 21st Century," J. Food Prot., Apr. 2007, 70(4):1041-1053.

Thanatuksorn et al., "Effects of ball-milling on the glass transition of wheat flour constituents," J. Sci. Food Agric., Dec. 2008, 89:430-435.

Torlak et al., "Inactivation of Cronobacter by gaseous ozone in milk powders with different fat contents," Int. Dairy J., Oct. 2013, 32(2):121-125.

Tsuang et al., "Studies of photokilling of bacteria using titanium dioxide nanoparticles," Artif. Organs, Feb. 2008, 32(2):167-174.

UMN.edu [online], "Intense Pulsed Light for Food Safety," available no later than Mar. 5, 2019, retrieved on Aug. 17, 2023, retrieved from URL<https://iplforfoodsafety.cfans.umn.edu/>.

Vetrimani et al., "Inactivation of lipase and lipoxygenase in cereal bran, germ and soybean by microwave treatment," Lebensm. Wiss. u. Technol., Jan. 1992, 25(6):532-535.

Williams et al., "Effects of Ultraviolet Radiation on the Gram-Positive Marine Bacterium Microbacterium maritypicum," Curr. Microbiol., Jun. 2007, 55:1-7.

Yang et al., "Infrared heating for dry-roasting and pasteurization of almonds," J. Food Eng., Dec. 2010, 101(3):273-280.

Zhang et al., "Microwave induced degradation of parathion in the presence of supported anatase- and rutile-$TiO_2$/AC and comparison of their catalytic activity," Chem. Eng. J., Sep. 2013, 231:84-93.

Zhong et al., "Microwave photocatalytic degradation of Rhodamine B using $TiO_2$ supported on activated carbon: Mechanism implication," J. Environ. Sci. (China), 2009, 21(2):268-272.

\* cited by examiner

DISINFECTING MATERIALS WITH INTENSE PULSED LIGHT AND CATALYTIC MICROWAVE-ASSISTED DECONTAMINATION

CROSS-REFERENCE TO RELATED APPLICATIONS

This application claims the benefit of U.S. Patent Application Nos. 62/819,040 filed Mar. 15, 2019; 62/883,557 filed Aug. 6, 2019; and 62/883,915 filed Aug. 7, 2019, all of which are incorporated by reference herein in their entirety.

STATEMENT OF GOVERNMENT INTEREST

This invention was made with government support under Grant No. 2016-68003-24850 awarded by the U.S.D.A. The government has certain rights in the invention.

TECHNICAL FIELD

This invention relates to systems and methods for disinfecting particulate materials with intense pulsed light and catalytic-assisted microwave-assisted decontamination.

BACKGROUND

Microorganisms can be a source of contamination in particulate materials. These microorganisms, which can be difficult to eliminate, can cause illness and economic loss. Disinfection of particulate materials with traditional thermal methods (e.g., hot air or steam heating) can damage physical, chemical, biological, and organoleptic properties of particulate materials. Moreover, treatment of bulk and packaged materials is typically ineffective and inefficient due to poor conductive heat transfer. Thus, effective methods are needed to inactivate microorganisms in particulate materials.

SUMMARY

Figure 1A:
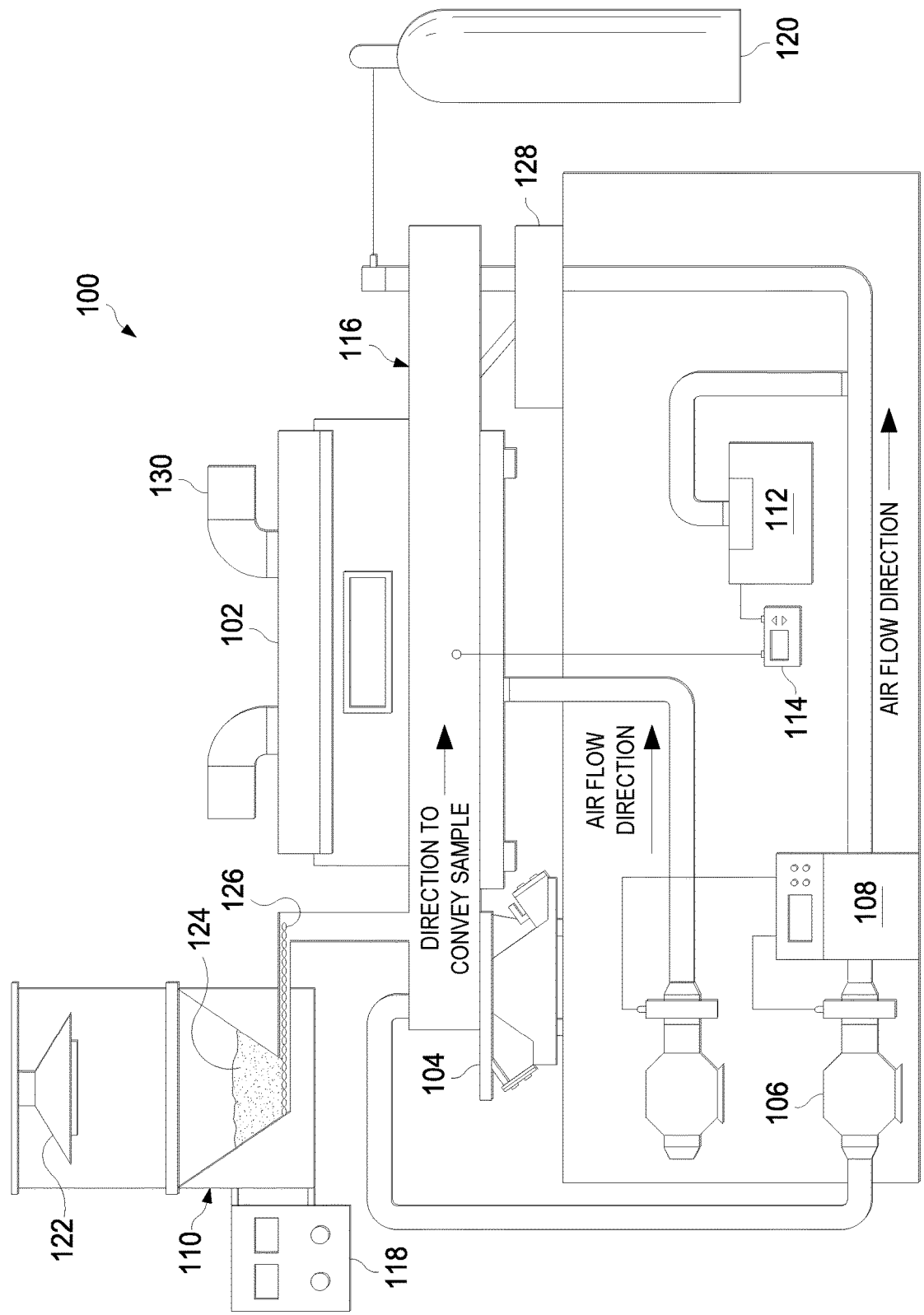
FIG. 1A depicts a system for disinfecting particulate materials with intense pulsed light (IPL) in the presence of a photocatalyst.

Systems and methods described herein provide scalable nonthermal treatments for safely and effectively disinfecting particulate materials with intense pulsed light (IPL) and a photocatalyst (catalytic IPL, or "cIPL") under controlled environmental conditions, as well as catalytic-assisted microwave decontamination ("cMAD"). cIPL causes less chemical (e.g. oxidative) and physical (e.g. thermal) damages to foods that other methods of pasteurization. Pulsed light has greater penetration depth than continuous ultraviolet (UV) light. Moreover, pulsed light can be high in intensity (0.01 to 50 J $cm^{-2}$) with short pulsed duration (100-500 µs). The intensity of the pulsed light can be 20000 times as high as the energy of solar light. As such, cIPL can be more efficient, rapid, and energy efficient than catalytic UV treatment. cIPL treatment described herein does not leave residual compounds or use external chemicals, such as disinfectants and preservatives, and can be used for a wide range of microorganisms, including bacteria, spores and viruses.

In a first general aspect, disinfecting particulate material includes combining the particulate material with a photocatalyst to yield a mixture, irradiating the mixture for a length of time with pulses from a light source having broadband emission spectrum between 190 nm-1100 nm to yield an irradiated mixture, and separating the photocatalyst from the disinfected mixture to yield the disinfected particulate matter. Irradiating the mixture inactivates microorganisms in the mixture to yield a disinfected mixture.

Implementations of the first general aspect may include one or more of the following features.

The particulate mixture includes a particulate food product or pharmaceutical product. In some examples, the particulate mixture includes grains, dried dairy products, flour, seasonings, seeds, or any combination thereof. The microorganisms may include bacteria, fungi, viruses, protozoa, algae, spores associated therewith, or any combination thereof.

The photocatalyst can be disposed on a substrate to yield a photocatalytic substrate. The photocatalyst may include titanium dioxide. A weight ratio of the photocatalyst to the photocatalytic substrate is typically in a range of 1:1 to 1:100. The substrate can be a polymer, a metal, or a metal oxide. In some cases, the substrate is selected from the group consisting of polyethylene, quartz, silica, stainless steel, polystyrene, silicon carbide, aluminum oxide, and zirconium oxide.

Irradiating the mixture for a length of time includes conveying the mixture under the pulsed ultraviolet radiation. The length of time is typically in a range of about 1 second to about 60 seconds. A frequency of the pulses is in a range of about 0.1 Hz to about 20 Hz. A duration of pulses is in a range of about 50 µs to about 70,000 µs. A voltage of the pulses is in a range of about 1000 V to about 3000 V. An energy of the pulses is up to about 2500 J/pulse.

In a second general aspect, a system for disinfecting particulate material includes a pulsed light source having a broadband emission spectrum in a range between about 190 nm and about 1100 nm, a chamber defining a cavity optically coupled to the pulsed light source, a humidifier, a fan, and one or more sensors. The chamber includes a conveyor configured to accept the particulate material and arranged such that the pulses emitted by the pulsed light source irradiate the particulate material on the conveyor.

Implementations of the second general aspect may include one or more of the following features.

The second general aspect may include a controller operatively coupled to the pulsed light source, the conveyor, the humidifier, the fan, and the one or more sensors. The one or more sensors may include a temperature sensor, a humidity sensor, and an anemometer.

In some implementations, a frequency of the pulses emitted by the pulsed light source is in a range of about 0.1 Hz to about 20 Hz. A duration of the pulses emitted by the pulsed light source is typically in a range of about 50 μs to about 70,000 μs. A voltage of the pulses emitted by the pulsed light source is typically in a range of about 1000 V to about 3000 V. In some cases, an energy of the pulses emitted by the pulsed light source is up to about 2500 J/pulse.

The conveyor comprises a photocatalyst and is configured to be irradiated with pulses emitted by the pulsed light source. In some cases, the second general aspect includes a surface coated with, including, or formed of a photocatalyst, wherein the surface is configured to reflect or concentrate pulses emitted by the pulsed light source to enhance disinfection of the particulate material on the conveyor.

In a third general aspect, disinfecting particulate material includes contacting the particulate material with a photocatalyst, and during the contacting, irradiating the particulate material, the photocatalyst, or both for a length of time with a pulsed irradiation from a light source having a broadband emission spectrum between about 190 nm and about 1100 nm. Irradiating the particulate material inactivates microorganisms in the particulate material to yield a disinfected particulate material.

Implementations of the third general aspect may include one or more of the following features.

The third general aspect may include separating the disinfected particulate material from the photocatalyst.

In a fourth general aspect, disinfecting a material includes combining the particulate material with a photocatalyst to yield a mixture, irradiating the mixture for a length of time with microwave radiation to yield an irradiated mixture, and separating the photocatalyst from the disinfected mixture to yield the disinfected particulate matter. Irradiating the mixture inactivates microorganisms in the mixture to yield a disinfected mixture.

Implementations of the fourth general aspect may include one or more of the following features.

In some cases, the particulate material is combined with a microwave absorber. The microwave absorber may include silicon carbide. The mixture may be irradiated with ultraviolet radiation. Irradiating the mixture for a length of time may include discretely irradiating the mixture for at least a first length of time and a second length of time, not exceeding a selected length of time and not exceeding a selected maximum temperature. In some cases, the selected maximum temperature is about 60° C. The selected length of time may be about 60 seconds.

The photocatalyst can be disposed on a substrate to yield a photocatalytic substrate. A weight ratio of the particulate material to the photocatalytic substrate is typically in a range of 1:1-3:1 or 1:1 to 100:1. The substrate may include a polymer, a metal, or a metal oxide. In some cases, the substrate is selected from the group consisting of polyethylene, quartz, silica, stainless steel, polystyrene, silicon carbide, aluminum oxide, and zirconium oxide.

In a fifth general aspect, a system for disinfecting particulate material includes a microwave radiation source, an electrodeless discharge lamp, a chamber defining a cavity operatively coupled to the microwave radiation source and the electrodeless discharge lamp, a humidifier, a fan, and one or more sensors. The chamber may be configured to accept the particulate material and arranged such that the microwave radiation and the electrodeless discharge lamp irradiate the particulate material.

Implementations of the fifth general aspect may include one or more of the following features.

In some cases, the one or more sensors include a thermocouple. In some cases, the fifth general aspect further includes a controller. The controller may be operatively coupled to the thermocouple and configured to initiate microwave radiation of the particulate material without exceeding a selected temperature. In certain cases, the controller is configured to irradiate the particulate material for a length or time not to exceed a selected length of time.

The details of one or more embodiments of the subject matter of this disclosure are set forth in the accompanying drawings and the description. Other features, aspects, and advantages of the subject matter will become apparent from the description, the drawings, and the claims.

DETAILED DESCRIPTION

Systems and methods described herein provide scalable nonthermal treatments for safely and effectively disinfecting particulate materials with intense pulsed light (IPL) and a photocatalyst under controlled environmental conditions, as well as catalytic-assisted microwave decontamination. Suitable photocatalysts include titanium dioxide ($TiO_2$). Examples of particulate materials that may be disinfected with such systems and methods include food products (e.g., grains, dairy, powders, flour, seasonings, seeds), pharmaceutical products, and cosmetic products. The particulate materials may be in a naturally occurring form (e.g., kernels or seeds) or may be processed to yield a desired particulate form (e.g., powders). As described herein, "disinfecting" includes inactivating microorganisms, including bacteria, fungi (e.g., yeasts and molds), viruses, protozoa, and algae, as well as spores associated with these microorganisms. Examples of bacteria that can be inactivated include *C. sakazakii*, *E. faecium*, and *B. cereus*. Disinfecting the particulate materials is achieved without damage (e.g., without thermal damage) or destruction of the particulate materials.

FIG. 1A depicts a system 100 for disinfecting particulate materials (e.g., inactivating pathogens from powdered foods and pharmaceutical products) with high-power, short-duration pulses of light (intense pulsed light (IPL)) and a photocatalyst (e.g., titanium dioxide). The system includes an IPL source 102 (e.g., an inert gas flash lamp), a vibratory feeder 104, flow fans coupled 106 with a thermostatic circulating water bath 108, a volumetric feeder 110, an humidifier/dehumidifier 112 (e.g., an ultrasonic humidifier/dehumidifier), and one or more sensors 114 (e.g., temperature sensor, humidity sensor, anemometer). In some cases, the system includes a conveyor 116. The system 100 typically includes a controller 118 operatively coupled to one or more components of the system, such that particulate materials are disinfected by the system continuously and automatically. The system may include or be coupled to an inert gas source 120, such as a nitrogen source. Process parameters include characteristics of the sample to be treated, transport and dispersion of samples, light intensity, pulse power, pulse width, pulse frequency, total number of pulses, residence time, energy received by the sample, sample temperature, and water activity and relative humidity of the sample.

In one implementation, the IPL source has a broadband emission spectrum in a range of about 200-1250 nm or about 190-1100 nm (e.g., including, overlapping, or encompassing this range). In one example, an IPL source is a broad spectrum light source including ultraviolet (UV), visible (VL), and infrared (IR) radiation. One example of a suitable IPL source is a xenon lamp. Parameters of the IPL source can be adjusted, including pulse rate (e.g., about 0.1-20 Hz), pulse duration (e.g., about 50-70,000 µs), voltage (e.g., about 1000-3000 V), and energy (e.g., up to about 2500 J/pulse). Feed rate of the particulate material can be adjusted by adjusting auger speed in the volumetric feeder. Residence time of the particulate material under the IPL source can be adjusted as appropriate. In some examples, a typical residence time is in a range of 5-60 seconds.

The photocatalyst (e.g., $TiO_2$) can be coated on a substrate to yield a photocatalytic substrate. The method of coating can affect the resulting particle size and the activity of the photocatalyst. In some cases, the photocatalyst can be doped. In some cases, the photocatalyst is doped, for example, to turn originally UV responsive titanium dioxide to visible light responsive titanium dioxide by lowering the excitation energy level. The substrate may be in the form of particles of various shapes, including spheres. Suitable materials for the substrate include polyethylene, quartz, silica, stainless steel, polystyrene, silicon carbide, aluminum oxide, zirconium oxide, and other appropriate materials. In one example, the substrate is in the form of glass beads. A dimension (e.g., diameter, length, width, thickness) of the substrate may be in a range of nanometers to millimeters. In some implementations, the photocatalytic substrate is combined with the particulate material to yield a mixture to be irradiated by the IPL source.

In some cases, the substrate may facilitate separation of the photocatalytic substrate from the particulate material. In one example, the substrate includes magnetic particles, such that application of a magnetic field may be used to facilitate removal of the photocatalytic substrate from the disinfected particulate material. In some implementations, a weight ratio of the photocatalyst to the particulate material is in a range of 1:1 to 1:100 or lower. In one example, a weight ratio of photocatalyst (e.g., Degussa p25 Titanium Dioxide Nanopowder, Ni doped $TiO_2$ nanopowder, or S doped $TiO_2$ nanopowder) to photocatalytic substrate (e.g., $Al_2O_3$) is about 1:100. This ratio provides close contact between the particulate material and the photocatalyst, thereby promoting rapid and efficient disinfection when irradiated with UVC radiation. In some implementations, the photocatalyst is coated on a smooth or textured surface configured to contact the particulate material during the disinfection process (e.g., during irradiation of the particulate material with the IPL source).

In one example, a photocatalyst is coated on a conveyor 116 that translates the particulate material through the system. In some implementations, the system includes a photocatalytic surface (e.g., a sheet formed of, including, or coated with $TiO_2$) to reflect or concentrate light from the IPL to improve the effectiveness of inactivation. In some cases, this photocatalytic surface is configured to be in direct contact with the particulate material, which may include or be free of an added photocatalyst. In other cases, this photocatalytic surface is configured such that direct contact with the particulate material is avoided.

The antimicrobial effect associated with $TiO_2$ photocatalysis is believed to be due to the generation of electron hole pairs of strong redox capability on the $TiO_2$ surface by microwave irradiation, microwave plasma, microwave generated UV light, and the like, converting water, oxygen, and nitrogen into highly oxidative species such as hydroxyl radicals ($\cdot OH$), and superoxide ions ($O\cdot$), ($O_2\cdot-$), ($N\cdot$), and ($N_2\cdot-$) that are effective in killing microbes.

In one implementation, a process for disinfecting particulate materials with a system such as that depicted in FIG. 1A includes adjusting a temperature of the thermostatic circulating water bath 108 (e.g., 55-60° C.) and initiating operation of the flow fans 106. The particulate material to be disinfected 124 may be loaded into the volumetric feeder 110. In some cases, the volumetric feeder is environmentally controlled. An appropriate paddle speed may be selected to mix the particulate material and photocatalytic substrate. Use of the infrared heater 122 to heat the mixture of the particulate material and the photocatalytic substrate may be discontinued once the mixture reaches a desired temperature. Operation of the IPL source 102, the vibratory feeder 104, and auger 126 is initiated, and the mixture is conveyed under the IPL source. The disinfected mixture is collected in a disinfected container 128, and the photocatalytic substrate is separated from the disinfected particulate material. In some cases, the disinfected mixture may be subjected to one or more additional passes through the system 100. System 100 may include a UV light cooling system 130 proximate IPL source 102.

The system in FIG. 1A is typically configured to uniformly expose all surfaces of the particulate materials to be treated with IPL in the presence of a photocatalyst under controlled conditions (e.g., temperature, relative humidity) while meeting process requirements and preventing caking of and moisture loss from particulate materials. The high peak intensity, short pulse duration, recycling environmental control system, as well as the narrow and sealed configuration of the vibratory feeder contribute to a high inactivation effect and relatively low energy consumption. In addition, $TiO_2$ can be used as a photocatalyst in food and health-related industries, and different feed rate ranges can be implemented to satisfy requirements (e.g., safety requirements, organoleptic requirements, and the like) for the powdered food and pharmaceutical industries.

Figure 1B:
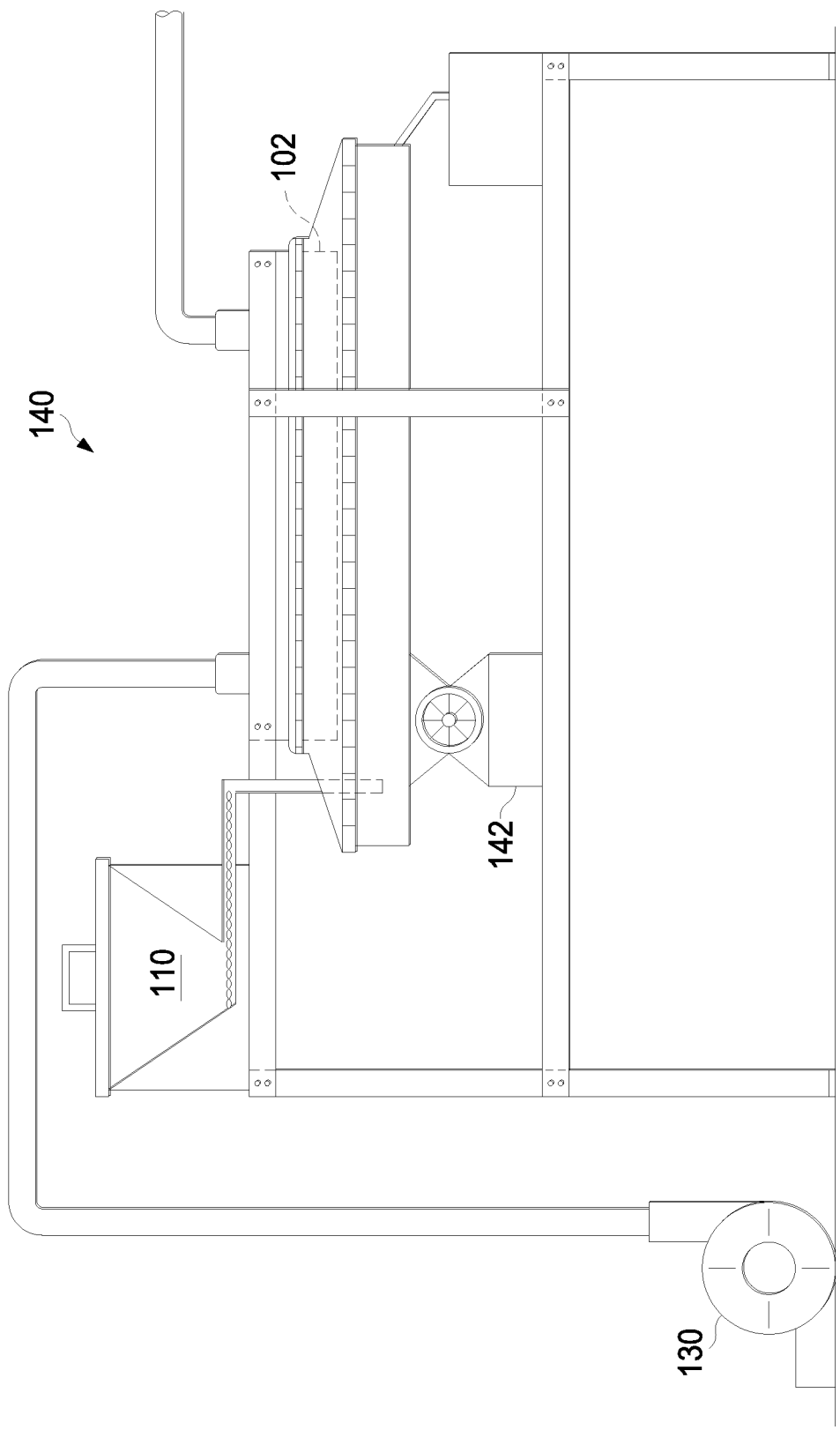
FIG. 1B depicts an IPL system having a closed system between the shaker bed and IPL light source.
Figure 1C:
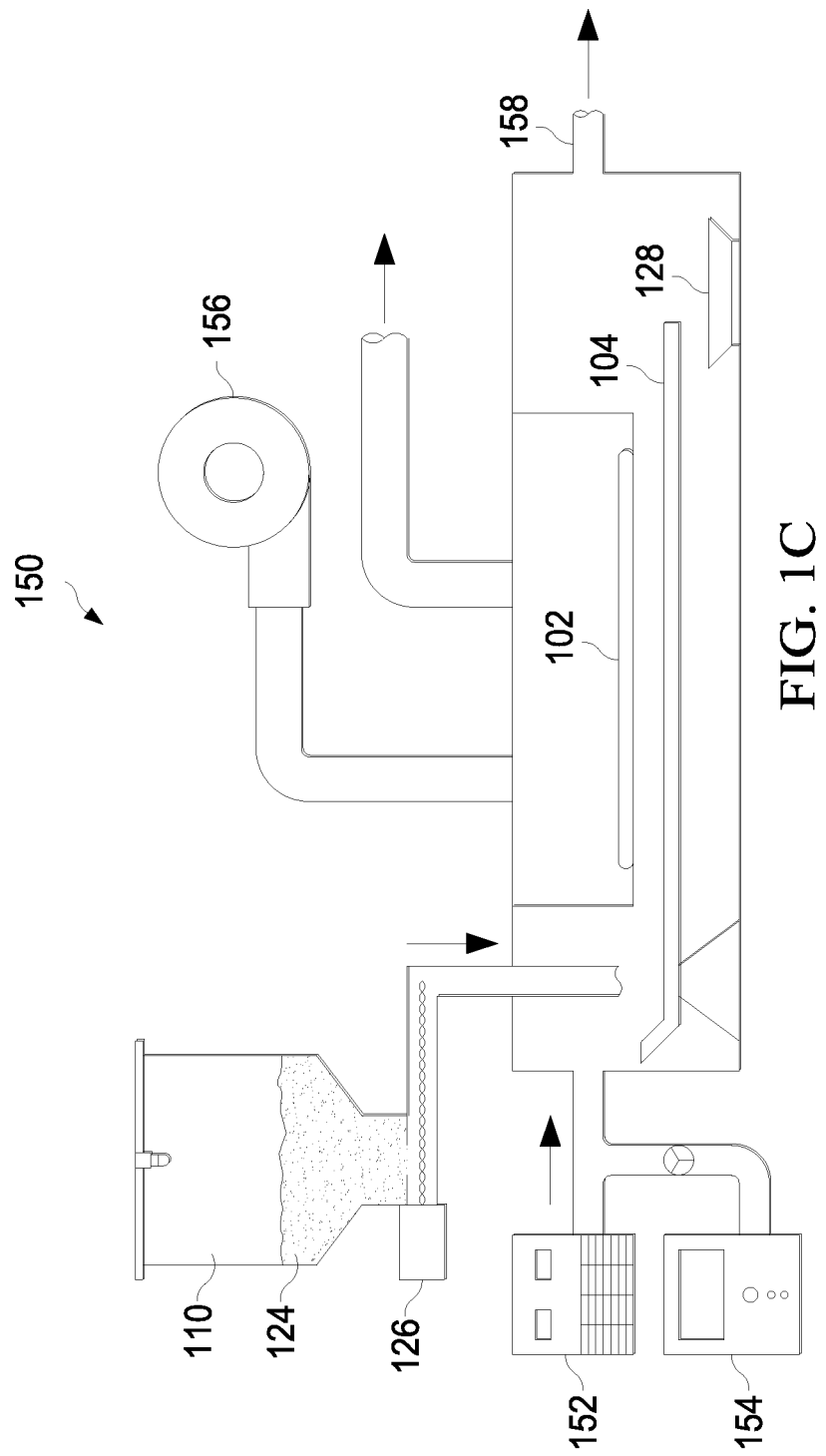
FIG. 1C depicts an IPL system having a temperature controller and a humidity controller.
Figure 1D:
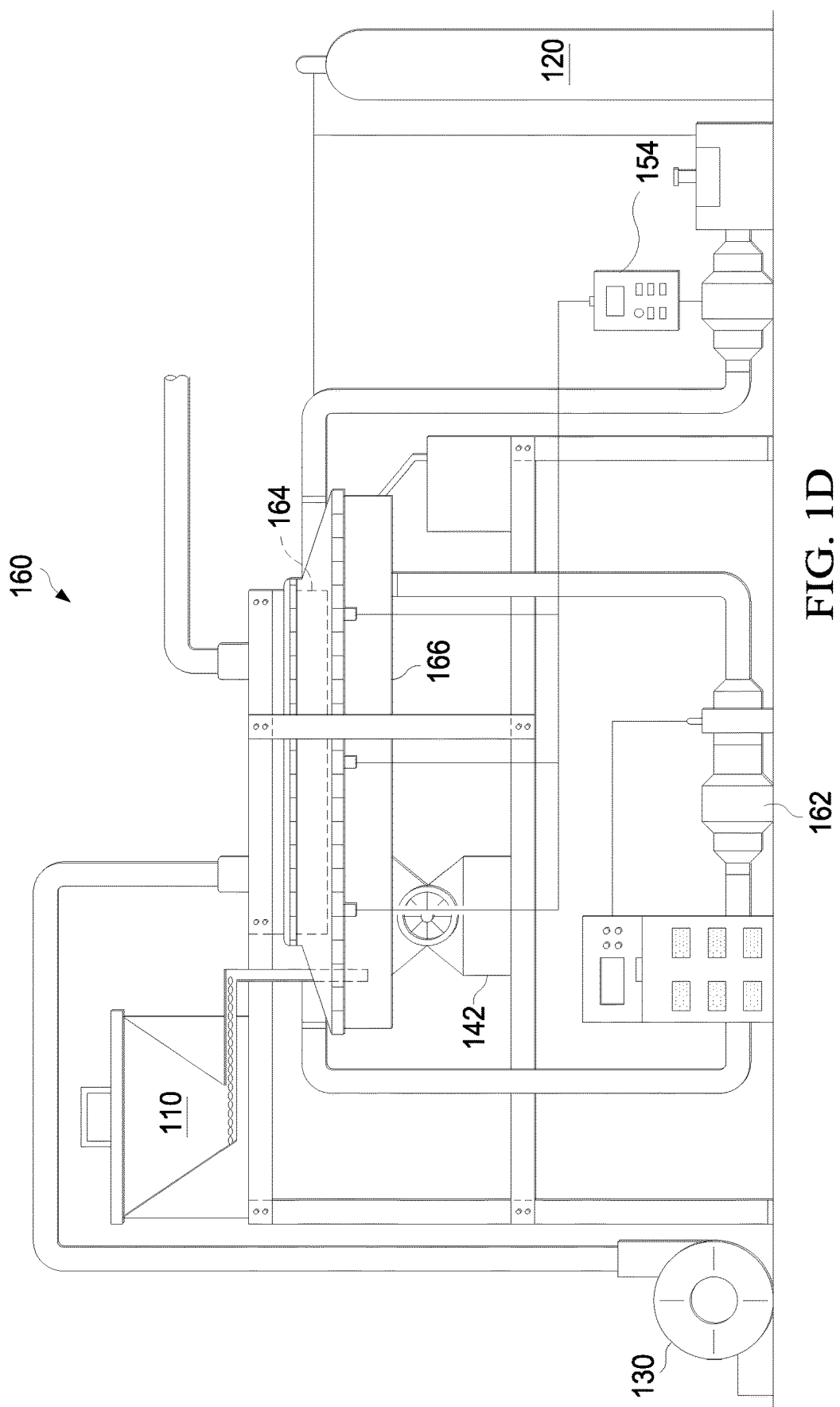
FIG. 1D depicts an IPL system having subsurface cooling, with nitrogen blanking added to extend substrate retention time.

Other IPL systems, such as those depicted in FIGS. 1B-1D, may have features in common with the IPL system of FIG. 1A. In some cases, other IPL systems include features in addition to those of the IPL system of FIG. 1A. FIG. 1B depicts an IPL system 140 having a closed system between the shaker 142 and IPL light source 102. FIG. 1C depicts an IPL system 150 having a temperature controller 152 and a humidity controller 154. IPL system 150 also includes a cooling fan 156 for the IPL source 102 and a system exhaust 166. FIG. 1D depicts an IPL system 160 having subsurface cooling system 162, flex insulation jacket 164, and a climate controlled region 166 for UV exposure. The IPL system 160 has nitrogen blanking to extend substrate retention time.

IPL can inactivate microorganisms by one or more processes, including photochemical damage, photothermal damage, and photophysical damage. In photochemical damage, the UV light portion of the pulsed light damages the DNA of bacteria by forming thymine dimers. Upon dimer formation, bacterial DNA cannot be unzipped for replication, and thus bacteria cannot reproduce. In photothermal damage, localized heating of bacteria is induced by pulsed light due to the difference in the heating/cooling rate and absorption characteristics of the bacteria and the surrounding matrix. Thus, the bacterial cell acts as a local vaporization center and may lead to membrane destruction and cell wall rupture. Thermal stress leads to rupture of microbial cells especially at higher flux densities (>0.5 J/cm$^2$). In photophysical damage, pulsed light is also expected to induce some physical disruption on microbial cellular structures (e.g., cell wall damage, membrane rupture, cytoplasm damage, or a combination thereof) due to the intermittent, high-intensity pulses, even when the temperature increase was negligible, suggesting that photophysical effects are a factor in microbial inactivation.

Figure 2:
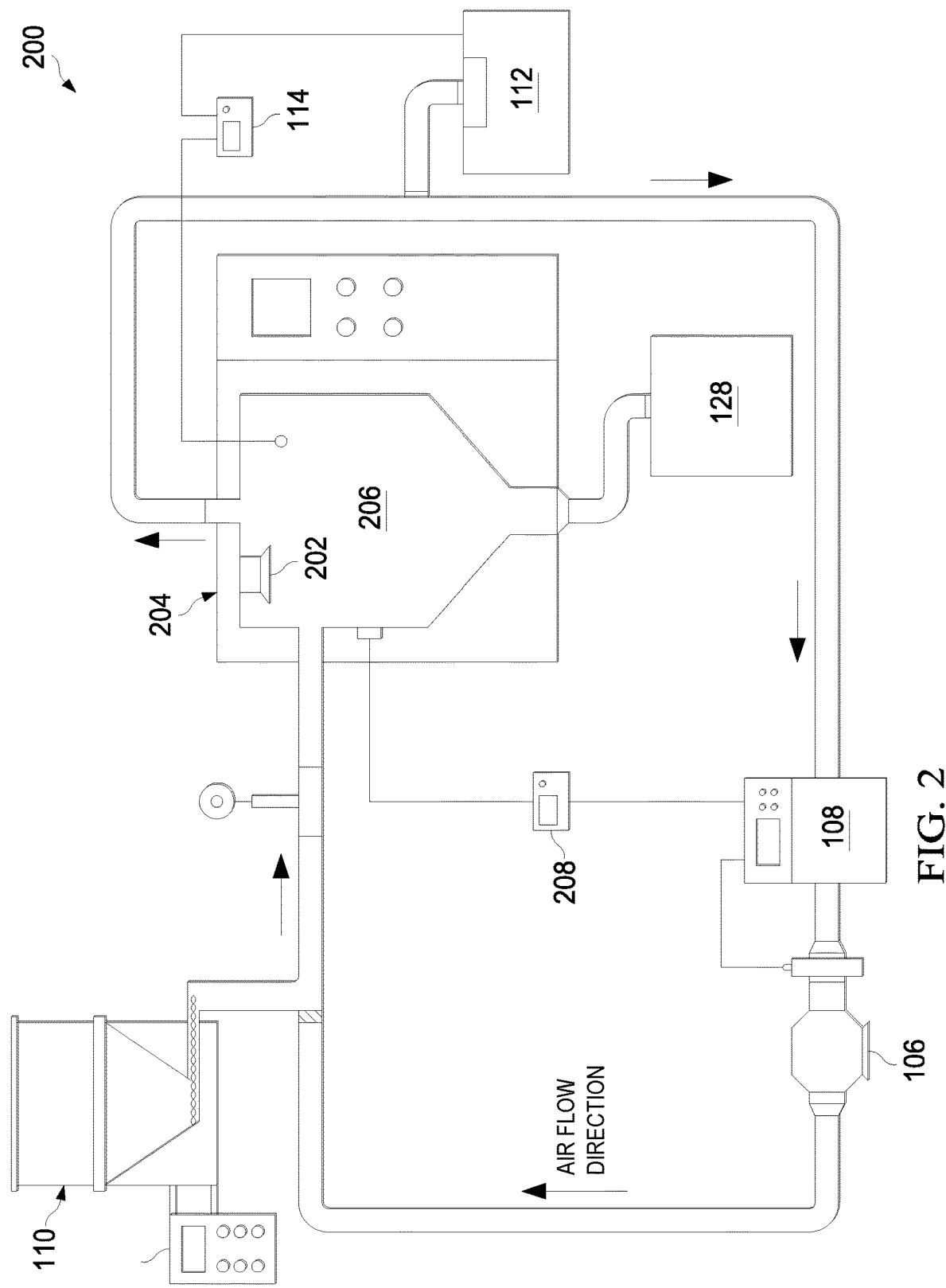
FIG. 2 depicts a system for catalytic microwave-assisted decontamination.

Microwave irradiation can be used to activate photocatalytic reactions in the presence of a photocatalyst (e.g., titanium dioxide). When used in combination with UV irradiation, microwave irradiation can enhance photocatalytic reactions due to a synergistic effect of the two irradiations. FIG. 2 depicts a catalytic microwave-assisted decontamination (cMAD) system 200 for inactivating microbes with microwave enhanced photocatalysis with an electrodeless discharge lamp (EDL) 202. The EDL generates UV/Vis radiation when placed in a microwave system 204. The cMAD system 200 may also include a cyclone reactor 206 and a temperature sensor 208 operatively positioned between the thermostatic water bath 108 and the cyclone reactor 206. A cMAD system, such as that depicted in FIG. 2, can be used for pasteurization of grains (e.g., wheat kernels, corn kernels, animal feed), seeds, seasonings, and ready to eat products (e.g., cookie dough). The cMAD system depicted in FIG. 2 can be modified for microbial inactivation in non-particulate produce and food items (e.g., fruits, vegetables, and pizza). In one example, to ensure flour safety, the system depicted in FIG. 2 can be used to inactivate microbes in wheat kernels before the kernels are milled. The cMAD or cIPL processes can be incorporated into the grain processing prior to milling or granulation.

Materials to be treated in a cMAD system can be combined with a photocatalyst as described with respect to FIG. 1A. The photocatalyst can be coated on a substrate, coated on a conveyor that translates the material through the system, or both. In some implementations, the cMAD system includes a photocatalytic surface (e.g., a sheet formed of, including, or coated with $TiO_2$) to reflect or concentrate light to improve the effectiveness of inactivation. In some cases, this photocatalytic surface is configured to be in direct contact with the material, which may include or be free of an added photocatalyst. In other cases, this photocatalytic surface is configured such that direct contact with the particulate material is avoided.

In some implementations, a photocatalyst can be coated onto the surface including pore surface of the microwave absorbent (e.g., solid or foam silicon carbide). Microwave heating of foods depends on the presence of polar materials such as water. In one example, the moisture content of wheat and wheat flour ranges from 13% to 18%. The moisture content of bacteria is in the range of 50-60%. If bacteria on the surface of wheat kernels are exposed to microwaves, it is believed that the bacteria absorb more microwave energy than the food matrix. As such, microorganisms become a local vaporization center and generate steam in the form of a microbubble. A momentous overheating may contribute to microbial inactivation, while maintaining flour functionality. In $TiO_2$ photocatalysis, light of wavelengths below a certain threshold can generate electron hole pairs of strong redox capability on the $TiO_2$ surface, converting water and oxygen into highly oxidative species such as hydroxyl radicals (·OH), and superoxide ions (O·) and ($O^{2·-}$) that are effective in killing microbes. Microwave irradiation is also capable of activating $TiO_2$ photocatalysis reactions. When used in combination with UV irradiation, microwave irradiation can significantly enhance the photocatalysis reactions possibly due to a synergistic effect of the two irradiations.

A fluidized bed can facilitate uniform exposure of wheat kernels to microwave treatment with SiC and $TiO_2$ and mixing. Application of silicon carbide (SiC) can enhance an efficient microwave absorbance, to improve the heating efficiency and control heating rate and temperature combining with wheat tempering. $TiO_2$ and modified $TiO_2$ catalysis allows decontamination of food products (e.g., wheat kernels) with minimal negative impact on the quality of the food product. Immobilization of catalysts enable easy recovery and reuse of the catalysts. Wheat kernels (e.g., after a tempering step) allow moisture on the surface to activate the microbes to the vegetative state more easily to be inactivated. Implementing cMAD right after or during tempering may help achieve bacterial inactivation and may improve the tempering process as well. SiC can be used to assist uniform microwave irradiation and microwave assisted microplasma generation for photocatalysis.

The overall temperature of the food matrix may be maintained below 60° C., while the temperature of the microbes (e.g., bacteria) exceeds 60° C., thereby inactivating the microbes. Microwave heating of wheat below 60° C. is understood to inactivate lipase and lipoxygenase activities, thereby extending the shelf life, without causing significant damage to flour functionality and baked quality. Microwave destruction of microbes or enzymes can be understood by one or more of the following mechanisms: selective heating, electroporation, cell membrane damage, and magnetic field coupling. Among them, the selective heating theory indicates that the microorganisms are selectively heated as discussed above. Electroporation, membrane rupture, and magnetic field coupling cause cellular membrane damages including the leakage, rupture, or disruption of cellular materials. cMAD processes described combine low temperature microwave heating with a photocatalyst (e.g., $TiO_2$) and an optional microwave absorbent (e.g., SiC) to effectively reduce microbial counts by 3-5 logs while maintaining the functionality of wheat and wheat flour.

Referring to FIG. 2, materials to be decontaminated are provided to a volumetric feeder 110 and advanced to a vessel 206 (e.g., a cyclone reactor). An EDL 202 is positioned in the vessel 206. A microwave system 204 provides microwave radiation to the vessel 206, thereby irradiating the materials to be decontaminated and activating the EDL 202. The materials to be decontaminated can be irradiated with one or more applications of microwave radiation. In one example, the materials to be decontaminated are irradiated for a first length of time while a temperature of the materials is monitored. When a first selected temperature (e.g., 60° C.) is reached, irradiation can be discontinued until the materials have cooled to a second selected temperature. Once the second selected temperature is reached, irradiation can begin again until the first selected temperature is reached again. This process can be repeated until a selected cumulative time of radiation (e.g., 60 s) is reached. The first selected temperature, second selected temperature, and selected cumulative time of radiation can be adjusted based on the material to be decontaminated.

Treated materials advance to the sample collector 128. The cMAD system 200 includes a temperature sensor 208 to monitor the temperature of the materials in the vessel 206 during treatment. The temperature sensor is operatively coupled to a controller in thermostatic circulating water bath 108, and application of microwave radiation can be controlled such that a maximum temperature, a maximum time of irradiation, or both is not exceeded. In some cases, the cMAD system 200 includes a humidity sensor 114, a humidifier 112, or both. In some cases, the cMAD system includes a blower 106 (e.g., a fin fan blower).

In one example, the cMAD system can be used to facilitate uniform exposure of the materials to be treated (e.g., wheat kernels) to microwave treatment with a microwave absorbent (e.g., SiC), a photocatalyst (e.g., $TiO_2$), or both. The cMAD system can provide continuous treatment for disinfection of materials (e.g., wheat grains). The cMAD system provides a method to enhance efficient microwave absorbance, improve the heating efficiency, and control heating rate and temperature using a microwave absorbent (e.g., silicon carbide) combined with tempering of the materials to be treated. The cMAD system provides a method to catalytically inactivate microorganisms using $TiO_2$ as a photocatalyst under microwave treatments. The reactivity of the catalysts can be improved with the presence of a photocatalyst under microwave microplasma conditions. The catalysts can be recovered and reused.

EXAMPLES

Bacteria Inoculum Preparation and Water Activity Adjustment

*Cronobacter sakazakii* (ATCC 29544), *Enterococcus faecium* (NRRL B-2354), and *Bacillus cereus* strain ATCC 14579 were inoculated onto NFDM (Land O'Lake, Inc., Arden Hills, MN) and wheat flour (General Mills Operations, Inc., Golden Valley, MN). *C. sakazakii, E. faecium,* and *B. cereus* were revived from frozen culture (–80° C.) onto tryptic soy agar (Neogen, Lansing, MI) supplemented with 0.6% (wt/vol) yeast extract (TSAYE; Sigma-Aldrich, St. Louis, MO), and stored at 4° C. 200 g of powder sample was transferred to a stainless-steel mixing bowl (30 cm in diameter). A 50 mL reagent sprayer (Fisher Scientific, Waltham, MA) was employed to spray 4 mL of bacterial cell mixture evenly onto samples. The nitrogen gas (3 psi) was used as a carrier gas. Samples were homogenized with a stainless-steel whisk to ensure a uniform distribution of inoculum on samples. Inoculated powders were subsequently transferred to desiccators (Thermo Fisher Scientific, Waltham, MA). Then the inoculated NFDM powder samples were adjusted to a water activity level of 0.25±0.2 by equilibrating in 25° C. Lithium chloride (Sigma-Aldrich, St. Louis, MO) for 7-10 days prior to the IPL treatment. The inoculated wheat flour samples were adjusted to a water activity level of 0.43±0.2 by equilibrating in 25° C. potassium carbonate for 7-10 days prior to the IPL treatment (Greenspan, 1977). The water activity level was tested with an Aqualab PawKit (Decagon Devices, Inc., Pullman, WA). The initial populations of *Cronobacter sakazakii* (ATCC 29544), *Enterococcus faecium* (NRRL B-2354), and *Bacillus cereus* (ATCC 14579) on these samples were around 7.8 $log_{10}$ CFU/g, 7.5 $log_{10}$ CFU/g, and 7.4 $log_{10}$ CFU/g, respectively.

Immobilization of $TiO_2$ on Glass Beads 0.2 mm diameter-glass beads (Sigma-Aldrich, St. Louis, MO) were etched with hydrofluoric acid (5%) for 24 h to create a rough contacting surface with $TiO_2$ slurry. 200 Ml $TiO_2$ slurry was made using 1.5 g $TiO_2$ powder (99.5% Sigma-Aldrich, St. Louis, MO)). The etched glass beads were subsequently placed in $TiO_2$ slurry for 20 min. In the meantime, a magnetic flea was employed to enable the uniform distribution of $TiO_2$ slurry on the surface of etched glass beads. Then the coated glass beads were transferred to a porcelain crucible, placed in an oven for 1.0 h at 150° C., and subsequently transported to a 500° C. furnace for another 2 h. Distilled water was then used to remove the free $TiO_2$ particles of the surface of coated $TiO_2$ beads.

Intense Pulsed Light and Ultraviolet Treatment

A X-1100 steripulse-XL system (Xenon Corporation, Woburn, MA) including a 76-cm linear xenon flash lamp, a sealed model-66C vibratory feeder (Eriez Manufacturing Co., Erie, PA), two 6-inch 390 CFM inline duct mixed flow fans connected with a thermostatic circulating water bath (LabX, Midland, ON, Canada), a Model-105 volumetric feeder (Tecnetics Industries, Inc., St. Paul, MN), an ultrasonic humidifier/dehumidifier, a nitrogen gas tank, an infrared heater, and an X-1100 power/control module, such as that depicted in FIG. 1, was employed. The output spectra of the IPL source are from 190 nm-1100 nm. The system allows the operators to adjust a variety of parameters including the pulse rate (0.3-14.0 Hz), pulse duration (50-7000 us), voltage (1000-3000 V), and energy (up to 2433 J/pulse). Feed rate of the powder samples can be adjusted by adjusting auger speed in volumetric feeder. Inoculated powdered foods such as NFDM and wheat flour were conveyed through the vibratory feeder under the different parameters of IPL with a residence time of 28 or 60 seconds. Regarding the IPL+$TiO_2$ mixture, the weight ratio of powdered sample and $TiO_2$ glass bead is ~1:100.

The detailed sample loading and process included the following steps. (1) Two flow fans were turned on after the temperature of the thermostatic circulating water bath achieved 55-60° C., the flow rate of cooling air was set at 54 $m^3$/h, and the flow rate of subsurface cooling air was set at 40.8 $m^3$/h. The valve of the nitrogen tank was subsequently opened and the flow rate was set at ~6 L/min, allowing at least 5 minutes to purge the air out of the IPL vibratory chamber and all connections. (2) Powdered samples were loaded into the environment-controlled volumetric feeder. (3) An appropriate paddle speed was set to mix the samples during heating with an infrared heater. The infrared heater was designed to automatically shut down when the samples were heated to the designed temperature. (3) The IPL source, vibratory feeder, and auger were started in order. The powdered samples were conveyed under the IPL source. (4) The powdered samples were collected using a disinfected container.

Measurements of the IPL Fluence, Temperature, and Flow Rate

A Vega laser power meter (Ophir Optronics Inc., Wilmington, MA) equipped with a PE-50C pyroelectric energy sensor (Ophir Optronics Inc., Wilmington, MA) was employed to measure the fluence received by the powdered samples during IPL treatments, the pyroelectric sensor was placed in the center of the vibratory feeder. The IPL source was raised to 10 cm to monitor the energy received at the height of 8 cm as the height of the energy sensor was 2 cm. The interval time of preventing the sensor from overheating is 30 s among each treatment. The temperature profiles of the powdered samples linked to the IPL treatment were monitored using a non-contact infrared thermometer with laser targeting (Cen-Tech, Montessori, NV). The temperatures of the powdered samples were immediately measured before and after each treatment. The air flow rate in chamber and subsurface were measured using a traceable hot wire anemometer (Control company, Friendswood, TX). All measurements were conducted at least in triplicate.

Particle Size Measurement

A LS 13 320 laser diffraction particle size analyzer (Beckman Coulter, Inc, Brea, CA) was employed to measure the particle size of NFDM and wheat flour samples. The powder samples were analyzed before and after IPL or UVC treatment. Five grams of the powder particles were randomly collected from each IPL treatment. All experiments were conducted in triplicate. The particle size of powdered samples was recorded and expressed in the unit of diameter (μm).

Color and Temperature Measurements

The quality of NFDM can be determined by color measurement. The color change of powdered food was measured by a chroma meter (Minolta CR-400, Minolta, Osaka, Japan). Three spots of each powdered sample were randomly selected for the color measurements. Color difference (ΔE) of powdered sample after IPL or UVC treatment was calculated using the chroma meter. The scale of ΔE can be categorized as not noticeable (0-0.5), slightly noticeable (0.5-1.5), noticeable (1.5-3.0), and well visible (3.0-6.0) (Gurol et al., 2012). All experiments were conducted in triplicate. The temperature profiles of powdered samples during treatments were monitored using a non-contact infrared thermometer with laser targeting (Cen-Tech, Montessori, NV).

Microorganism Enumeration

One gram of NFDM or wheat flour sample was diluted in 0.1% (w/v) peptone serially. 100 μL of each diluted sample was surface plated onto different agar medium. Diluted *C. sakazakii* cells were spread onto HiCrome *Cronobacter* spp agar, modified (Sigma-Aldrich, St. Louis, MO), *E. faecium* cells were dispersed onto M-*Enterococcus* agar (HiMedia, Laboratories, LLC, Kennett Square, PA), and *B. cereus* using *Cereus* Selective agar (Sigma-Aldrich, St. Louis, MO). *C. sakazakii* and *E. faecium* plates were incubated at 37° C. for 48-72 hours prior to enumeration. With respect to *B. cereus*, a heat shock process (80° C. for 12 min) was applied before plating to remove the vegetative cells of *B. cereus*, and *B. cereus* plates were then incubated at 30° C. for 24-48 hours. Each bacteria colony plate was counted manually, and the number of bacteria colonies was then expressed as colony-forming units per gram (CFU/g).

Statistical Analysis

The results presented are averages of at least three independent experiments from each powdered sample and expressed as means±standard deviations (SD). Statistical analyses were developed using JMP Pro 13 (SAS Cary, NC). The analysis of variance (ANOVA) was conducted with significance level set to $p<0.05$.

Effect of IPL on Various Microorganisms in NFDM and Wheat Flour

Inactivation of microorganisms including *C. sakazakii* and *E. faecium* as a function of IPL frequency, voltage, and feed rate are shown in FIGS. 3A-3D. At the same voltage and feed rate levels, the results show that lower IPL frequency causes significantly higher $\log_{10}$ CFU/g reduction. This may be due to the higher energy density applied with lower IPL frequency. The energy density was ~0.291 J/cm²/pulse at 1 Hz, while the energy density was 0.021 J/cm²/pulse at 14 Hz. The energy density of IPL received by samples can be adjusted through adjusting the distance between the samples and lamp. Increasing energy density by reducing the frequency can be considered as an alternative method to improve the inactivation. A relatively low IPL frequency such as 1 Hz was applied to enhance the energy intensity for each pulse. In most cases, higher voltage induced higher inactivation than lower voltage. Higher peak intensity caused by higher voltage led to the same amount of fluence produced in shorter pulse duration (μs). For instance, the pulse duration was 342 μs at 3000 V and IPL pulsed frequency of 1 Hz. The pulse duration was 773 μs at 2200 V and IPL pulse frequency of 1 Hz. Therefore, the sterilization of IPL treatment can be attributed to factors including energy intensity per pulse and pulse duration. Overall, the inactivation decreased with increasing the feed rate from 4200 to 8100 g/h and 3600 to 7200 g/h for NFDM and wheat flour, respectively. The regulation was obvious especially for samples at relatively low IPL frequency. Further reducing the feed rate would not cause the significant increase of inactivation effect of IPL. The inactivation difference between these feed rates might be due the limited depth of the IPL penetration. High inactivation effect of IPL treatment is due at least in part to the rich UV component. The model X-1100 has substantially richer UV content than model Z-1000 shown in lamp spectrum. A high UV component has been found more effective for eliminating bacteria.

An IPL system such as that depicted in FIG. 1A is environmentally friendly, cost-effective, and efficient, achieving a *C. sakazakii* inactivation of ~3 $\log_{10}$ CFU/g and consuming only 7.13 J/cm². Factors other than high energy intensity contributing to the higher energy efficiency can be understood as follows. The width of the vibratory feeder was reduced from 30 to 18 cm. The narrower pathway was used to facilitate the IPL reflection to the samples and avoid energy waste. Higher voltage (2200-3000 V) applied in this IPL system is another factor that promotes inactivation efficiency. As discussed previously, the higher voltage results in shorter pulse duration and higher peak intensity of the IPL system. A feature of this enclosed gas recycling system enables most of the feed gas to be recycled while feeding or exhausting a small amount of fresh gas.

FIGS. 3A-3D show the effect of the IPL system on the inactivation of *C. sakazakii* and *E. faecium* in wheat flour and NFDM. The total fluence (energy flux) of each treatment is 7.13 J/cm² (28 s). The feed rate of NFDM at 4200 and 8100 g/h were associated with layer thicknesses of ~1.2 and 2.0 mm, respectively. The feed rates of wheat flour at 3600 and 7200 g/h were associated with layer thickness of ~1.2 and 2.0 mm, respectively. Error bars show standard deviation.

Temperature Profile and Particle Size

No obvious caking would be induced when amorphous powdered food is below the glass transition temperature ($T_g$). However, an undesirable agglomerated form of amorphous powdered foods might be generated as the sample temperature exceeds $T_g$. Unwanted caking of powdered foods inhibits the microorganism inactivation under the IPL treatments. Organoleptic qualities may also be affected. Samples of NFDM and wheat flour were treated with IPL and UVC treatments under a variety of attributes with a residence time of 28 s. The sample temperature and water activity are shown in Table 1. The final temperature of NFDM was controlled under 58° C. to avoid caking. With respect to wheat flour, although the $T_g$ of wheat flour exceeds 100° C., the final temperature was controlled under 58° C. in order to minimize the physical and chemical changes of wheat flour. As shown in Table 2, no significant change in particle diameter occurred for all sample treatments. This is due at least in part to the appropriate control of temperature and humidity.

TABLE 1

Temperature and water activity profiles of each treatment. (a) NFDM, the relative humidity (RH) in IPL chamber was maintained at 25-30% during the IPL treatment, (b) Wheat flour, the RH in IPL chamber was maintained at 35-40% during the IPL treatment.

|  | Initial temperature ± SD (° C.) | Final temperature ± SD (° C.) | Initial water activity level ± SD | Final water activity level ± SD |
|---|---|---|---|---|
| (a) | | | | |
| NFDM | | | | |
| 120 s-UVC | 55.2 ± 1.0A | 56.3 ± 0.8B | 0.25 ± 0.01C | 0.24 ± 0.01E |
| 1 | 55.9 ± 0.6A | 56.2 ± 0.6B | 0.26 ± 0.01C | 0.25 ± 0.01E |
| 2 | 55.2 ± 0.3A | 56.7 ± 0.6B | 0.25 ± 0.01C | 0.25 ± 0.01E |
| 3 | 55.9 ± 0.6A | 56.2 ± 0.6B | 0.26 ± 0.01C | 0.26 ± 0.01E |
| 4 | 56.1 ± 0.6A | 56.9 ± 0.6B | 0.27 ± 0.02C | 0.26 ± 0.01E |
| 5 | 55.2 ± 0.9A | 56.4 ± 0.8B | 0.24 ± 0.01C | 0.24 ± 0.01E |
| 6 | 54.9 ± 0.9A | 55.7 ± 1.2B | 0.25 ± 0.02C | 0.25 ± 0.01E |
| 7 | 55.9 ± 0.8A | 56.3 ± 0.5B | 0.26 ± 0.02C | 0.25 ± 0.01E |
| 8 | 55.2 ± 0.3A | 56.5 ± 0.9B | 0.24 ± 0.01C | 0.24 ± 0.01E |
| 9 | 55.9 ± 0.6A | 56.1 ± 0.8B | 0.25 ± 0.01C | 0.25 ± 0.01E |
| 10 | 55.4 ± 0.3A | 56.5 ± 0.5B | 0.24 ± 0.02C | 0.24 ± 0.01E |
| 11 | 55.5 ± 0.3A | 56.5 ± 0.9B | 0.24 ± 0.01C | 0.24 ± 0.01E |
| 12 | 55.9 ± 0.6A | 57.2 ± 0.5B | 0.25 ± 0.01C | 0.24 ± 0.01E |
| (b) | | | | |
| Wheat flour | | | | |
| 120 s-UVC | 54.2 ± 0.8A | 56.9 ± 1.1B | 0.40 ± 0.01D | 0.35 ± 0.01F |
| 1 | 54.9 ± 0.6A | 56.8 ± 0.6B | 0.40 ± 0.01D | 0.36 ± 0.01F |
| 2 | 54.2 ± 0.6A | 56.9 ± 0.9B | 0.40 ± 0.01D | 0.37 ± 0.01F |
| 3 | 54.9 ± 0.6A | 56.2 ± 1.1B | 0.39 ± 0.01D | 0.35 ± 0.01F |
| 4 | 54.1 ± 0.6A | 56.9 ± 0.6B | 0.41 ± 0.02D | 0.35 ± 0.01F |
| 5 | 54.2 ± 0.9A | 56.6 ± 0.8B | 0.39 ± 0.01D | 0.36 ± 0.01F |
| 6 | 54.4 ± 0.8A | 56.7 ± 0.9B | 0.40 ± 0.01D | 0.36 ± 0.01F |
| 7 | 54.5 ± 0.8A | 56.3 ± 0.5B | 0.40 ± 0.01D | 0.35 ± 0.01F |
| 8 | 54.5 ± 0.3A | 56.5 ± 0.8B | 0.39 ± 0.01D | 0.37 ± 0.01F |
| 9 | 53.9 ± 0.9A | 56.5 ± 1.3B | 0.41 ± 0.01D | 0.35 ± 0.01F |
| 10 | 54.6 ± 0.9A | 56.6 ± 0.9B | 0.41 ± 0.01D | 0.36 ± 0.01F |
| 11 | 54.7 ± 0.6A | 56.3 ± 0.8B | 0.41 ± 0.01D | 0.36 ± 0.01F |
| 12 | 54.7 ± 0.6A | 56.1 ± 0.5B | 0.41 ± 0.02D | 0.35 ± 0.01F |

TABLE 2

(a) The mean particle size of NFDM as a function of variable attributes. (b) The mean particle size of wheat flour as a function of variable attributes. The untreated powdered samples are taken as control.

|  | Voltage (V) | Feed rate (g/h) | Frequency (Hz) | Particle diameter (μm) |
|---|---|---|---|---|
| (a) NFDM | | | | |
| Control | NA | NA | NA | 50.13 ± 1.76a |
| 120 s-UVC | NA | NA | NA | 52.41 ± 0.68a |
| 1 | 3000 | 4200 | 1 | 52.08 ± 0.85a |
| 2 | 3000 | 4200 | 3 | 51.41 ± 1.92a |
| 3 | 3000 | 4200 | 14 | 49.58 ± 0.67a |
| 4 | 3000 | 8100 | 1 | 48.52 ± 2.03a |
| 5 | 3000 | 8100 | 3 | 53.38 ± 2.02a |
| 6 | 3000 | 8100 | 14 | 51.27 ± 0.98a |
| 7 | 2200 | 4200 | 1 | 51.52 ± 1.70a |
| 8 | 2200 | 4200 | 3 | 51.79 ± 0.59a |
| 9 | 2200 | 4200 | 14 | 51.71 ± 1.32a |
| 10 | 2200 | 8100 | 1 | 51.63 ± 0.73a |
| 11 | 2200 | 8100 | 3 | 51.15 ± 0.89a |
| 12 | 2200 | 8100 | 14 | 50.30 ± 1.75a |
| (b) Wheat Flour | | | | |
| Control | NA | NA | NA | 54.19 ± 0.99a |
| 120 s-UVC | NA | NA | NA | 55.34 ± 0.89a |
| 13 | 3000 | 3600 | 1 | 54.94 ± 1.32a |
| 14 | 3000 | 3600 | 3 | 52.95 ± 0.71a |
| 15 | 3000 | 3600 | 14 | 54.70 ± 0.35a |
| 16 | 3000 | 7200 | 1 | 53.53 ± 1.51a |
| 17 | 3000 | 7200 | 3 | 55.39 ± 1.20a |
| 18 | 3000 | 7200 | 14 | 55.46 ± 1.50a |
| 19 | 2200 | 3600 | 1 | 51.83 ± 3.20a |
| 20 | 2200 | 3600 | 3 | 52.41 ± 1.53a |
| 21 | 2200 | 3600 | 14 | 53.18 ± 2.20a |
| 22 | 2200 | 7200 | 1 | 55.47 ± 1.21a |
| 23 | 2200 | 7200 | 3 | 52.88 ± 1.89a |
| 24 | 2200 | 7200 | 14 | 53.62 ± 1.78a |

Data in the same column followed by the same uppercase letter are not significantly different (P > 0.05).

Color Change

Table 3 shows the color difference (ΔE) of NFDM and wheat flour after IPL and 120 s-UVC treatments. Microorganism inactivation among different IPL treatment conditions was compared. ΔE was affected by the attributes of voltage, feed rate, and IPL frequency. The results showed that the highest ΔE was observed at the conditions of 3000 V, feed rate of 4200 g/h, and frequency of 1 Hz. IPL frequency and feed rate affected ΔE of NFDM significantly, while the voltage did not significantly change the ΔE. (Three-way ANOVA within-group comparison: feed rate: p=0.04<0.05, Frequency: p=0.008<0.01, Voltage:

p=0.102>0.05.) To achieve ~3 log 10 CFU/g reduction of *C. sakazakii*, the IPL system caused less ΔE than earlier systems. The probable reasons may be due to the low IPL fluence applied. In addition, the nitrogen gas present may have acted a barrier to reduce the photo-oxidative process of NFDM from light treatment. In terms of IPL on wheat flour, no noticeable color difference was induced by IPL treatment (ΔE<0.5). Moreover, there was no significant difference among all IPL treated samples with respect to the effect of UV on the inactivation of *C. sakazakii* and *E. faecium* in NFDM and wheat flour. A significantly higher color difference change was observed using UV treatment than IPL treatment. (Tables 2 and 3, FIGS. 3A and 3C).

TABLE 3

Color difference (ΔE) of (a) NFDM and (b) wheat flour subjected to UVC and IPL treatments at various attributes.

| | Voltage (V) | Feed rate (g/h) | Frequency (Hz) | ΔE |
|---|---|---|---|---|
| (a) NFDM | | | | |
| 120 s-UVC | NA | NA | NA | 3.36 ± 0.28a |
| 1 | 3000 | 4200 | 1 | 2.49 ± 0.12b |
| 2 | 3000 | 4200 | 3 | 2.17 ± 0.16c |
| 3 | 3000 | 4200 | 14 | 1.94 ± 0.03d |
| 4 | 3000 | 8100 | 1 | 2.12 ± 0.08c |
| 5 | 3000 | 8100 | 3 | 1.99 ± 0.22cd |
| 6 | 3000 | 8100 | 14 | 1.79 ± 0.29cd |
| 7 | 2200 | 4200 | 1 | 2.27 ± 0.23bc |
| 8 | 2200 | 4200 | 3 | 2.02 ± 0.29cd |
| 9 | 2200 | 4200 | 14 | 1.82 ± 0.09d |
| 10 | 2200 | 8100 | 1 | 2.09 ± 0.16cd |
| 11 | 2200 | 8100 | 3 | 1.75 ± 0.15e |
| 12 | 2200 | 8100 | 14 | 1.58 ± 0.07e |
| (b) Wheat flour | | | | |
| 120 s-UVC | NA | NA | NA | 0.66 ± 0.22a |
| 13 | 3000 | 3600 | 1 | 0.23 ± 0.15b |
| 14 | 3000 | 3600 | 3 | 0.20 ± 0.11b |
| 15 | 3000 | 3600 | 14 | 0.22 ± 0.14b |
| 16 | 3000 | 7200 | 1 | 0.11 ± 0.10b |
| 17 | 3000 | 7200 | 3 | 0.10 ± 0.06b |
| 18 | 3000 | 7200 | 14 | 0.16 ± 0.14b |
| 19 | 2200 | 3600 | 1 | 0.19 ± 0.06b |
| 20 | 2200 | 3600 | 3 | 0.16 ± 0.06b |
| 21 | 2200 | 3600 | 14 | 0.10 ± 0.08b |
| 22 | 2200 | 7200 | 1 | 0.21 ± 0.10b |
| 23 | 2200 | 7200 | 3 | 0.21 ± 0.05b |
| 24 | 2200 | 7200 | 14 | 0.11 ± 0.06b |

Data in the same column followed by the same uppercase letter are not significantly different (P > 0.05). The data were expressed as the mean ± standard deviation of measurements made in triplicate.

Extended Treatment Time

The results discussed above suggested that the highest inactivation could be obtained at the voltage of 3000 V; IPL frequency of 1 Hz; feed rate of 4200 g/h and 3600 g/h for NFDM and wheat flour, respectively. To investigate the maximum inactivation ability of the IPL system, the IPL treatment time was extended to 60 s (feed rate of 2100 g/h and 1800 g/h for NFDM and wheat flour, respectively) on the conditions of these parameters. Table 4 shows enhanced *C. sakazakii*, *E. faecium*, and *B. cereus* spore inactivation are achieved for both NFDM and wheat flour samples after 60 s IPL treatment. Thus, this IPL system with controlled environment, appropriate IPL parameters, and conveying or agitation process provides a significant inactivation effect in powdered foods.

In terms of the effect of IPL in comparison with UVC on microbes in NFDM and wheat flour, the microorganism inactivation with IPL was significantly higher than that with UVC treatments. As discussed previously, less color change was induced with IPL than UVC to achieve a similar inactivation. Therefore, in some cases the IPL may be a more feasible technology to eliminate the pathogens in NFDM and wheat flour in the aspects of quality maintenance and inactivation effect.

Further extended IPL or UVC treatment time did not cause significantly higher inactivation. Cracks and pores are known to be present in all types of milk powder particles. Microbes on the surface are more readily eliminated than those hidden in open pores of powdered food with IPL or UVC treatment. Bacteria of the upper layers, inactivated with IPL, may prevent the rest of the sample from receiving the IPL. Therefore, limited IPL exposure may be received by the rest of the bacteria.

TABLE 4

Effect of 60 s-IPL and 120 s-UVC on inactivating *C. sakazakii*, *E. faecium*, and *B. cereus* inoculated in (a) NFDM and (b) wheat flour, respectively. The total fluence (energy flux) of 60s-IPL treatment is 17.46 J/cm$^2$. Data represent mean of at least triplicates ± one standard deviation.

(a)

| Treatment condition | Log reduction of microorganisms in NFDM (log CFU/g) | | |
|---|---|---|---|
| | *C. sakazakii* | *E. faecium* | *B. cereus* |
| 120 s-UVC | 2.14 ± 0.12A | 1.94 ± 0.59A | |
| 60 s-IPL | 3.97 ± 0.08B | 3.00 ± 0.04B | 1.68 ± 0.38 |

(b)

| Treatment condition | Log reduction of microorganisms in Wheat flour (log CFU/g) | | |
|---|---|---|---|
| | *C. sakazakii* | *E. faecium* | *B. cereus* |
| 120 s-UVC | 1.79 ± 0.11A | 2.94 ± 0.04A | |
| 60 s-IPL | 4.15 ± 0.07B | 3.31 ± 0.06B | 1.53 ± 0.21 |

Data in the same column of the same table followed by the same uppercase letter are not significantly different (P > 0.05).

Evaluation of Combined Disinfection Effects of IPL and Titanium Dioxide

Tables 4 and 5 show that significantly higher bacteria inactivation (*C. sakazakii* and *E. faecium*) in NFDM and wheat flour were achieved with IPL+TiO$_2$ than IPL only. Especially noteworthy was that this photocatalyst combined with IPL was able to lead to a significantly higher disinfection effect for *B. cereus* spore. Bacterial endospores are generally more resistant than the vegetative forms because of the increased cell wall thickness. The TiO$_2$ coated glass beads allow close contact between the catalyst and the microorganisms, thereby enhancing inactivation.

TABLE 5

Effect of 60 s-IPL + TiO$_2$ on inactivating *C. sakazakii*, *E. faecium*, and *B. cereus* inoculated in NFDM and wheat flour, respectively. The total fluence (energy flux) of 60 s-IPL treatment is 17.46 J/cm$^2$. Data represent mean of at least triplicates ± one standard deviation.

| Type of microorganism | Log reduction of microorganism (log CFU/g) | |
| --- | --- | --- |
| | NFDM | Wheat flour |
| *C. sakazakii* | 4.71 ± 0.07A | 5.42 ± 0.10B |
| *E. faecium* | 3.49 ± 0.01A | 4.95 ± 0.24B |
| *B. cereus* | 2.52 ± 0.10A | 2.80 ± 0.23A |

Data in the same row of the same table followed by the same uppercase letter are not significantly different (P > 0.05).

Figure 3A:
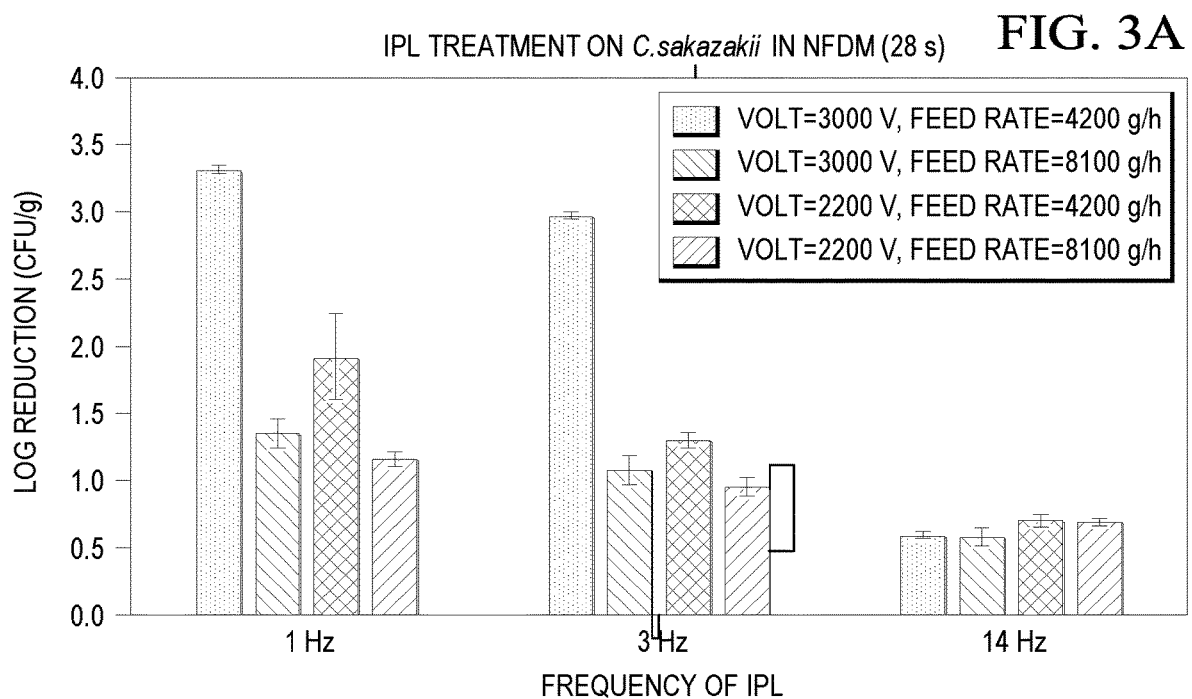
FIGS. 3A-3D show inactivation of microorganisms as a function of IPL frequency, voltage, and feed rate.
Figure 3B:
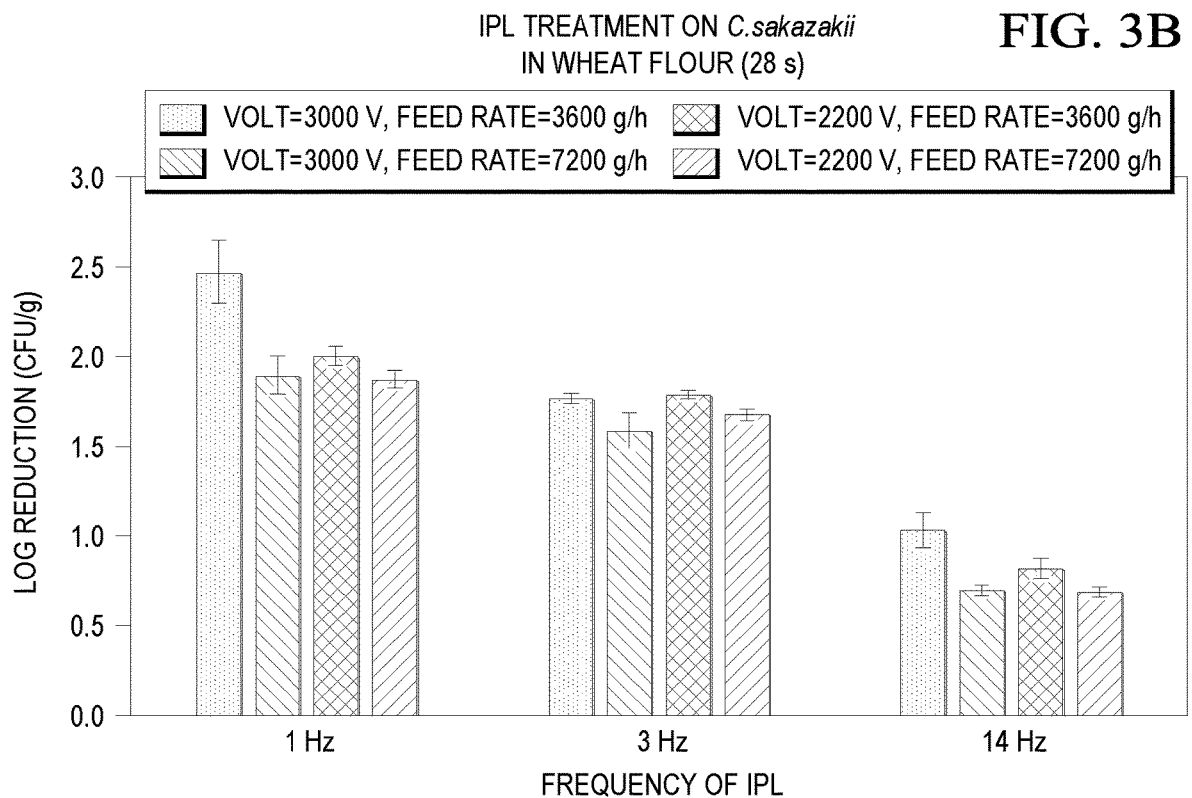
Figure 3C:
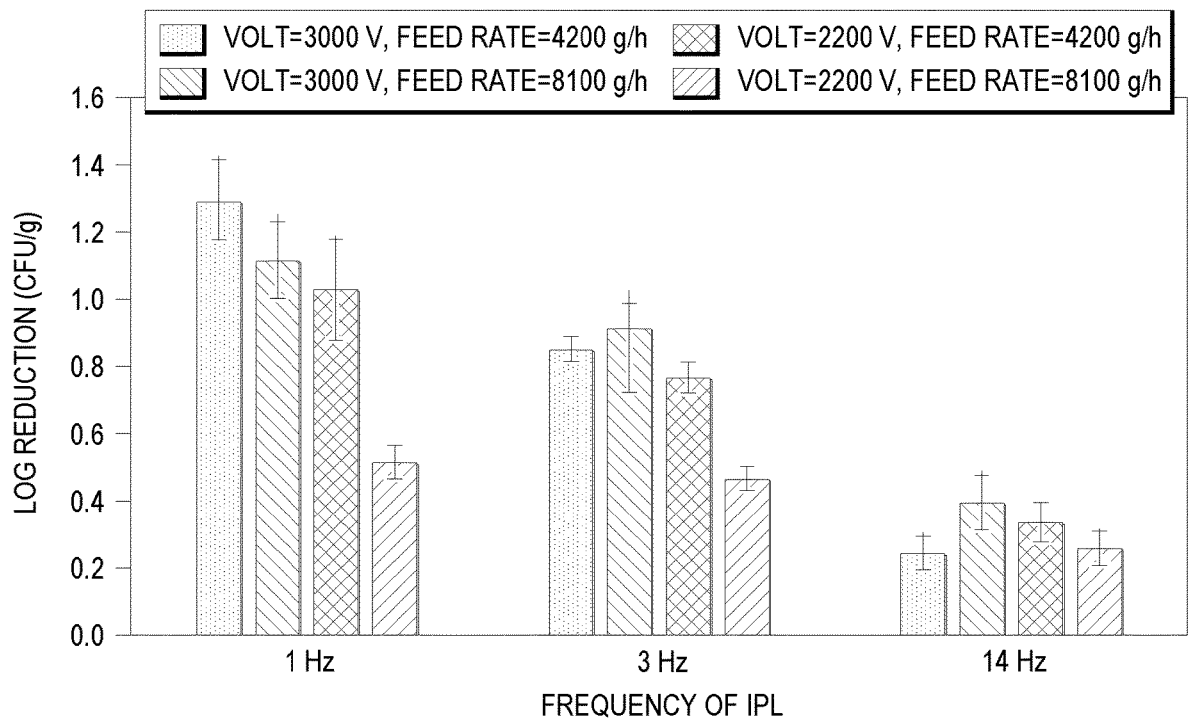
Figure 3D:
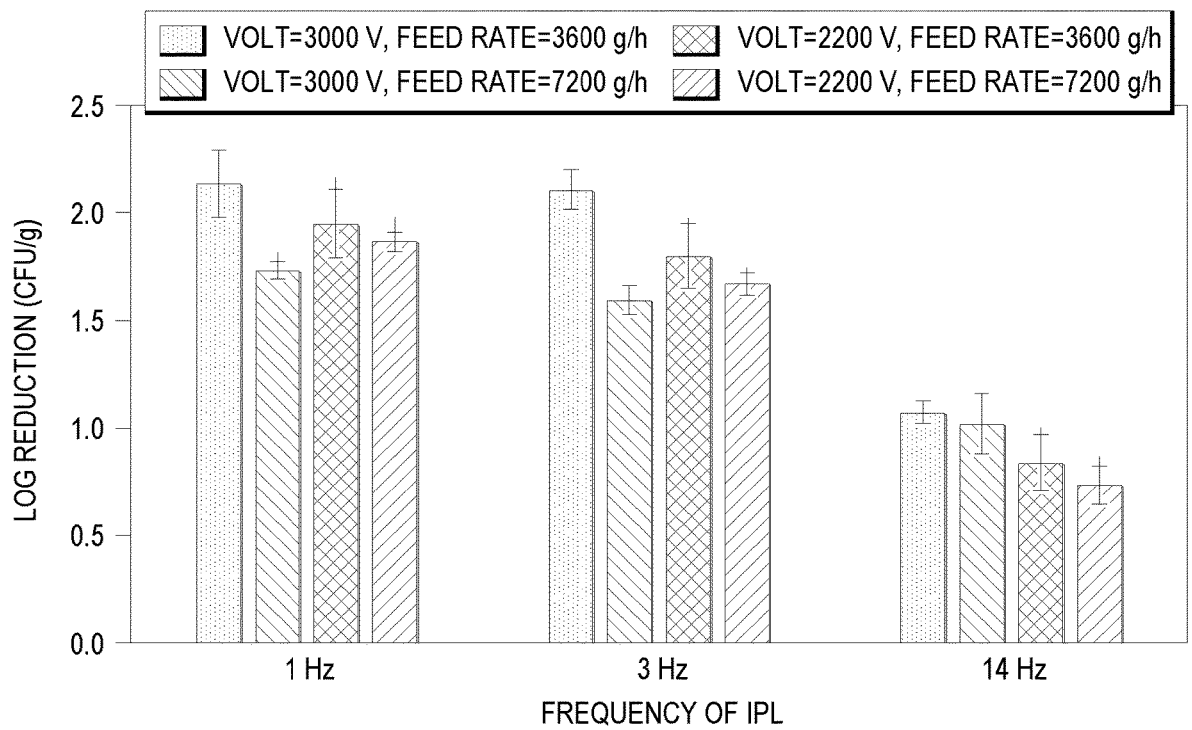
Figure 3E:
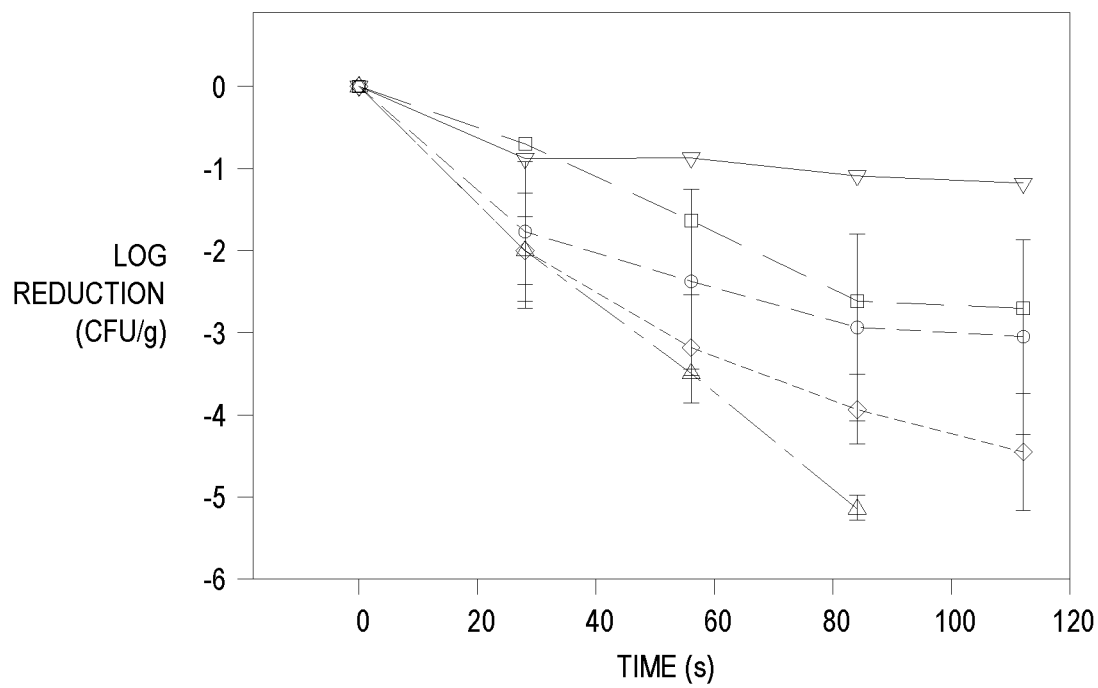
FIGS. 3E-3G show inactivation of microorganisms as a function of length of irradiation.

FIG. 3E shows log$_{10}$ CFU/g reduction for *Cronobacter sakazakii* ATCC 29544 as a function of time for non-fat dry milk, wheat flour, whole egg powder, egg white powder, and ground black pepper. One IPL pass is equal to 25 seconds. NFDM (n=11), Wheat flour (n=4), Egg whites (n=2), Whole egg (n=1), and Black pepper (n=1). Error bars are standard deviation.

Figure 3F:
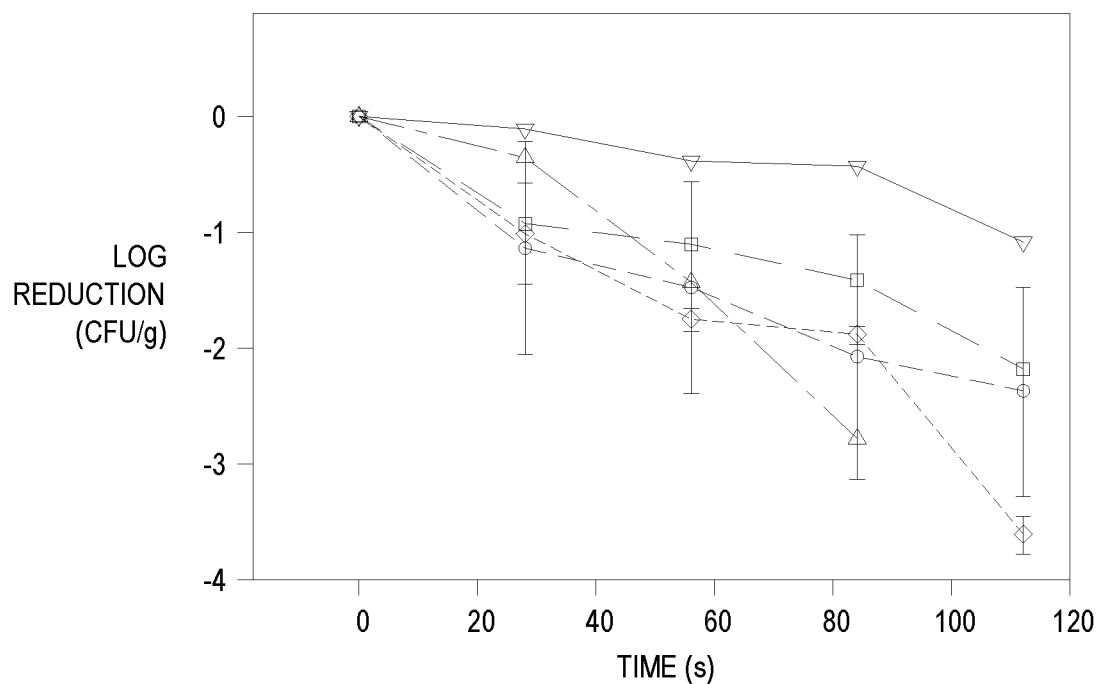

FIG. 3F shows log$_{10}$ CFU/g reduction for *Enterococcus faecium* NRRL B-2354 as a function of time for non-fat dry milk, wheat flour, whole egg powder, egg white powder, and ground black pepper. One IPL pass is equal to 25 seconds. NFDM (n=3), Wheat flour (n=4), Egg whites (n=2), Whole egg (n=1), and Black pepper (n=1). Error bars are standard deviation.

Figure 3G:
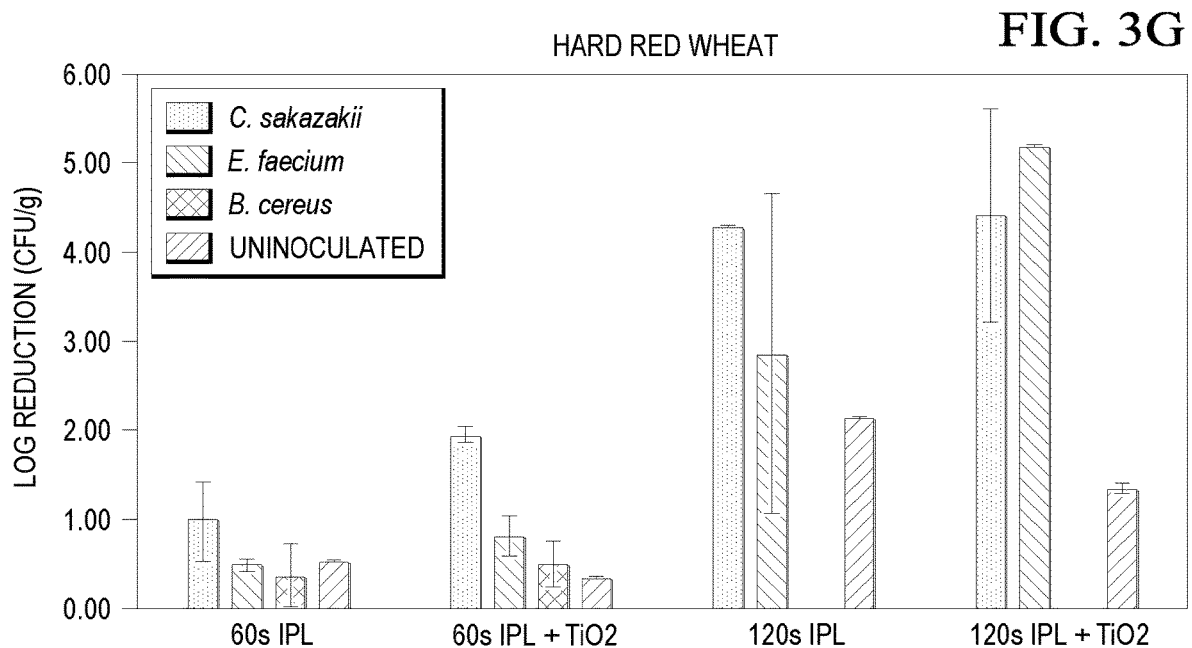

FIG. 3G shows log$_{10}$ CFU/g reduction for IPL on hard red wheat samples inoculated with *C. sakazakii, E. faecium*, or *B. cereus*, and as well as uninoculated (control) samples.

Figure 3H:
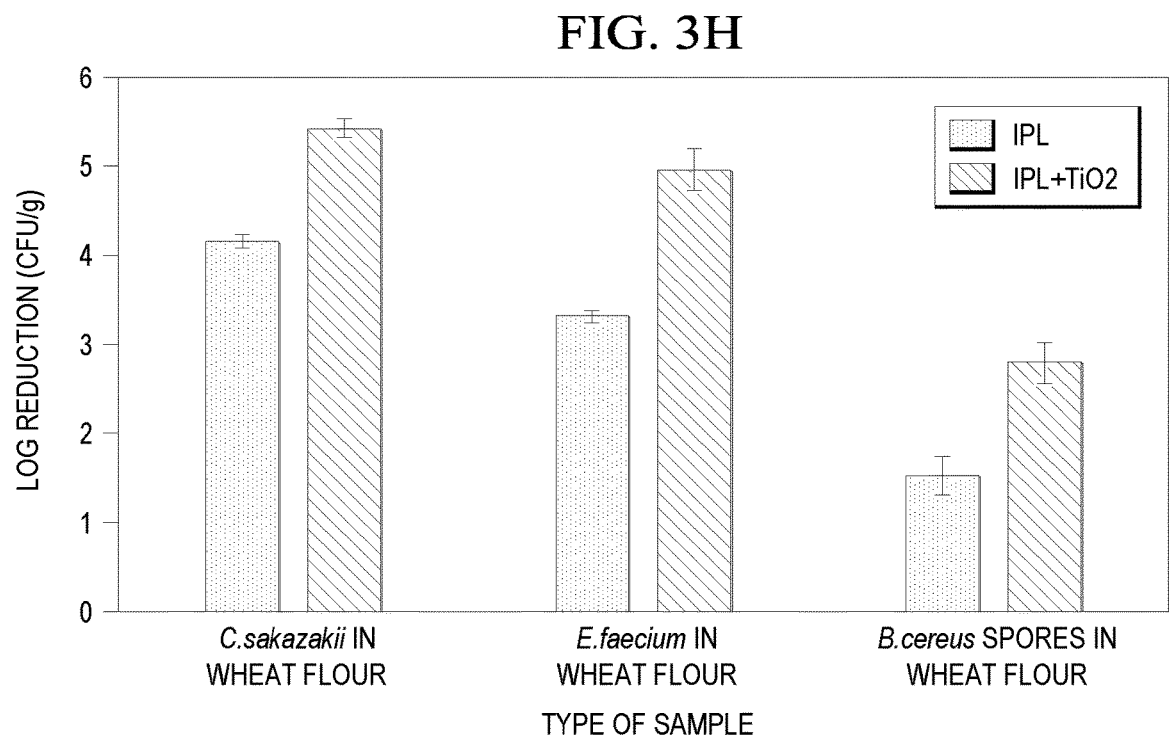
FIG. 3H shows inactivation of different microorganisms, with and without titanium dioxide, for different lengths of irradiation.
Figure 3I:
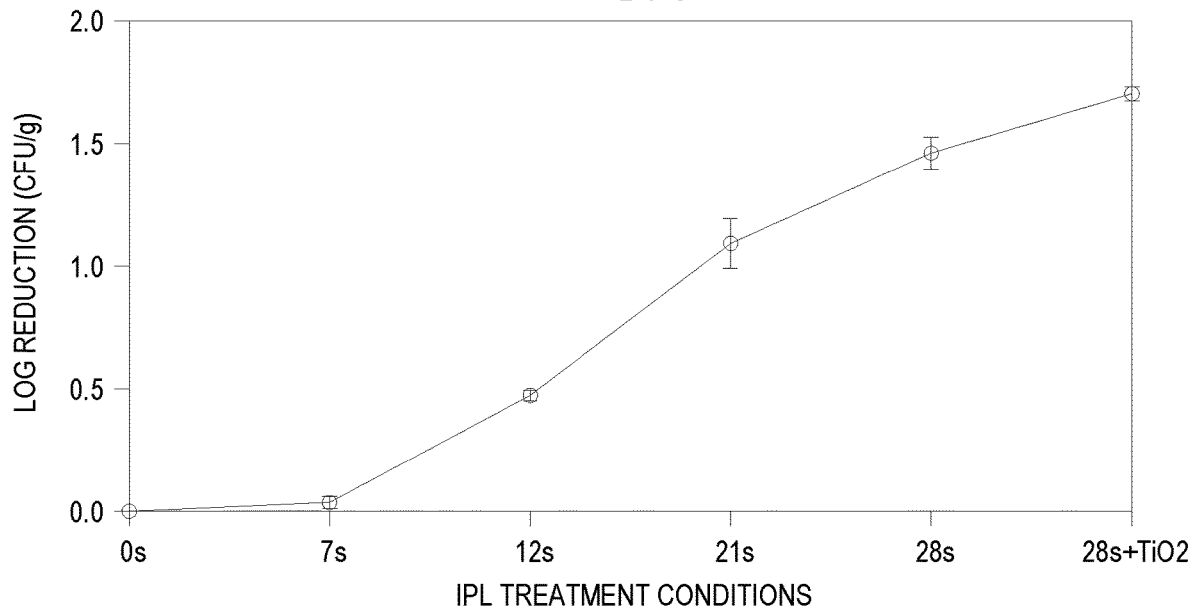
FIG. 3I shows the effect of IPL and cIPL on inactivating microorganisms inoculated in mesquite flour.

FIG. 3H shows log$_{10}$ CFU/g reduction for *C sakazakii* in wheat flour, *E. faecium* in wheat flour, and *B. cereus* spores in wheat flour with IPL alone and IPL in the presence of titanium dioxide. Pulse lengths were 60 s. The titanium dioxide was coated on 2 mm beads. The total fluence (energy flux) of 60 s-IPL treatment was 17.46 J/cm$^2$.

Wheat kernels were disinfected with IPL and cIPL (titanium dioxide) treatments. Table 6 shows log$_{10}$ CFU/g reduction for *C sakazakii* (IPL), *C sakazakii* (IPL+TiO$_2$), *E faecium* (IPL), *B. cereus* (IPL), and natural microorganisms (IPL+TiO$_2$).

TABLE 6

Disinfection of Wheat Kernels with cIPL

| Microorganism and Treatment Conditions | Log reduction (log CFU/g) |
| --- | --- |
| *C. sakazakii* (IPL) | 4.21 (120 s) |
| *C. sakazakii* (IPL + TiO$_2$) | 5.00 (120 s) |
| *C. sakazakii* (IPL) | 4.16 (120 s) |
| *C. sakazakii* (IPL + TiO$_2$) | 0.81 (60 s) |
| Natural microorganism (IPL + TiO$_2$) | 1.4 (120 s) |

Overall, the catalytic IPL treatment caused higher bacterial inactivation than IPL treatment. For wheat flour, synergistic effects of IPL and TiO$_2$ photocatalysis on microbial inactivation was studied. With TiO$_2$ photocatalysis, one additional log$_{10}$ reduction was achieved, bringing the total log reduction to 5.42±0.10 (*C. sakazakii*), 4.95±0.24 (*E. faecium*), and 2.80±0.23 (*B. cereus*) in wheat flour. With respect to wheat kernels, catalytic IPL resulted in higher microbial inactivation than that of IPL alone after 120 s. For mesquite flour, because of the dark color and low transparency of the samples, IPL induced 1.5 log$_{10}$ CFU/g reduction for *B. cereus* spores. Catalytic IPL caused 0.2 log$_{10}$ CFU/g reduction higher than IPL alone.

Microwave-Enhanced Photocatalysis for Inactivating Microbes

A domestic household microwave system (2450 MHz) with output power of 1000 W was adopted, such as that depicted in FIG. 2. Inoculated wheat kernels were placed in a porcelain crucible under the different parameters of microwave treatment with a residence time of 60 seconds. TiO$_2$-coated beads were prepared as described previously. The weight ratio of sample to TiO$_2$ coated glass bead was ~1:1 (10 g each of the samples and the TiO$_2$ coated beads). The inoculated wheat kernels and the TiO$_2$ coated beads were mixed uniformly in a porcelain crucible. After loading the samples in the microwave system, the microwave was turned on for about 30 s for the samples to reach to a temperature of about 60° C. The microwave was then turned off, and the samples were allowed to cool down to a temperature in a range of about 53-55° C., which took about 5-10 s. The microwave was then turned on again for another 5 s or so to reach a sample temperature of about 60° C. The process was repeated until the total treatment time reached 60 s. The temperature was monitored by thermocouple. After microwave treatment, the wheat kernels were separated from TiO$_2$ coated beads using a 2200 μm sieve.

Figure 4A:
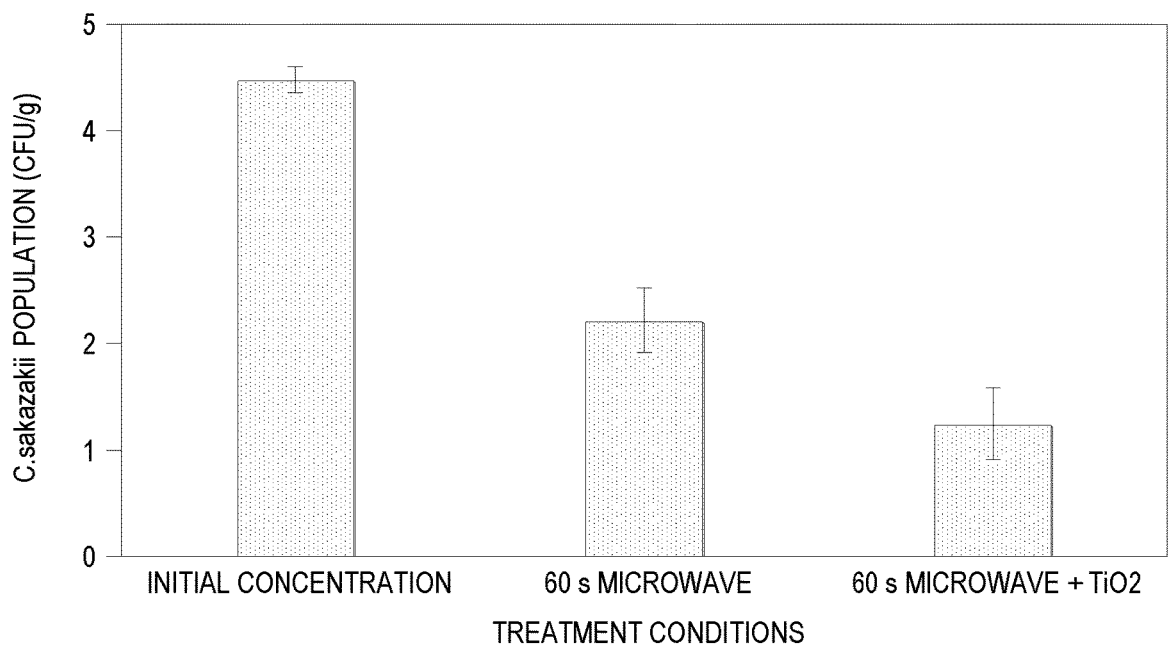
FIG. 4A shows the effect of microwave treatment conditions on *C. sakazakii* inoculated in wheat kernels.
Figure 4B:
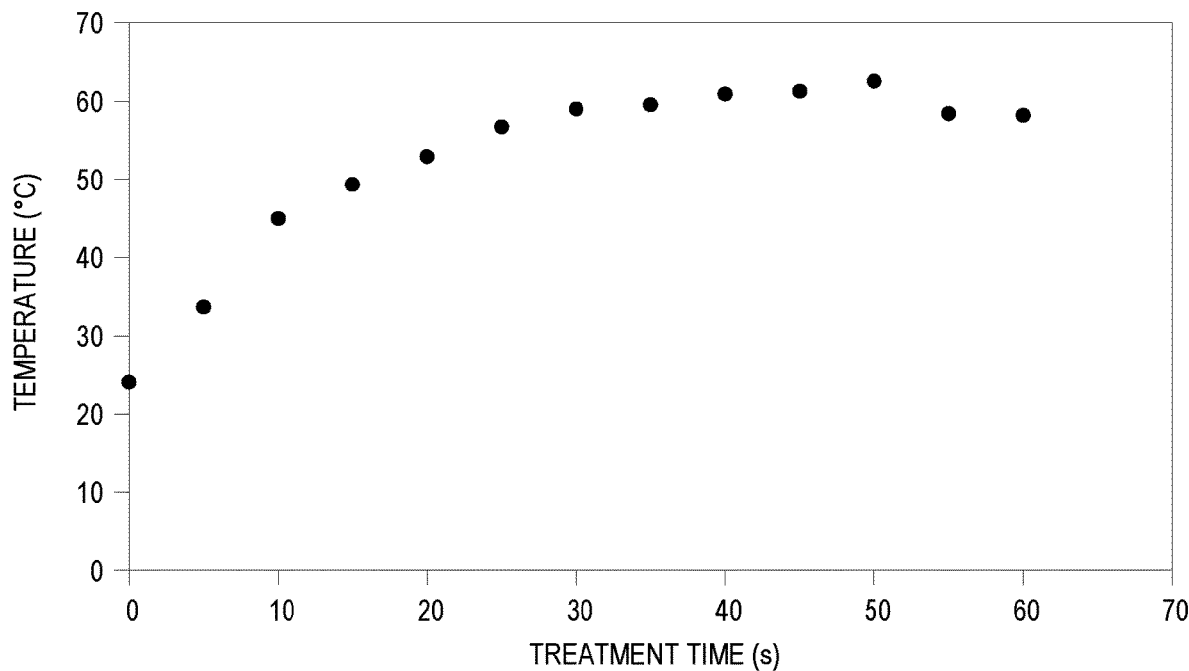
FIG. 4B shows temperature versus time for wheat kernels during microwave treatment with a photocatalyst.
Figure 4C:
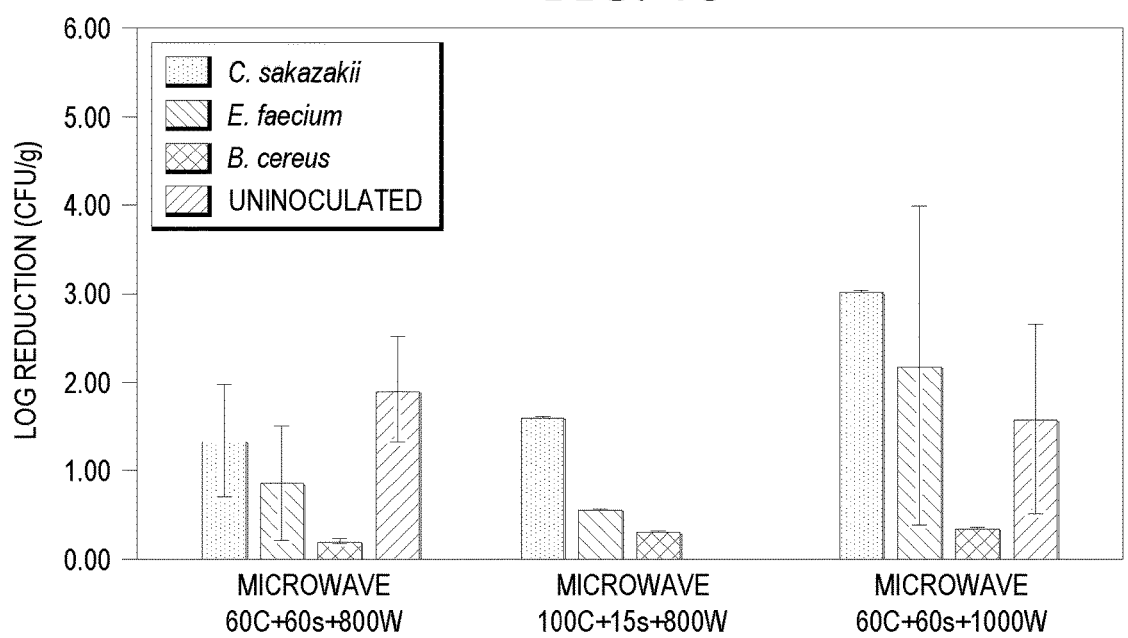
FIG. 4C shows the effect of microwave treatment on wheat kernels under different conditions.
Figure 4D:
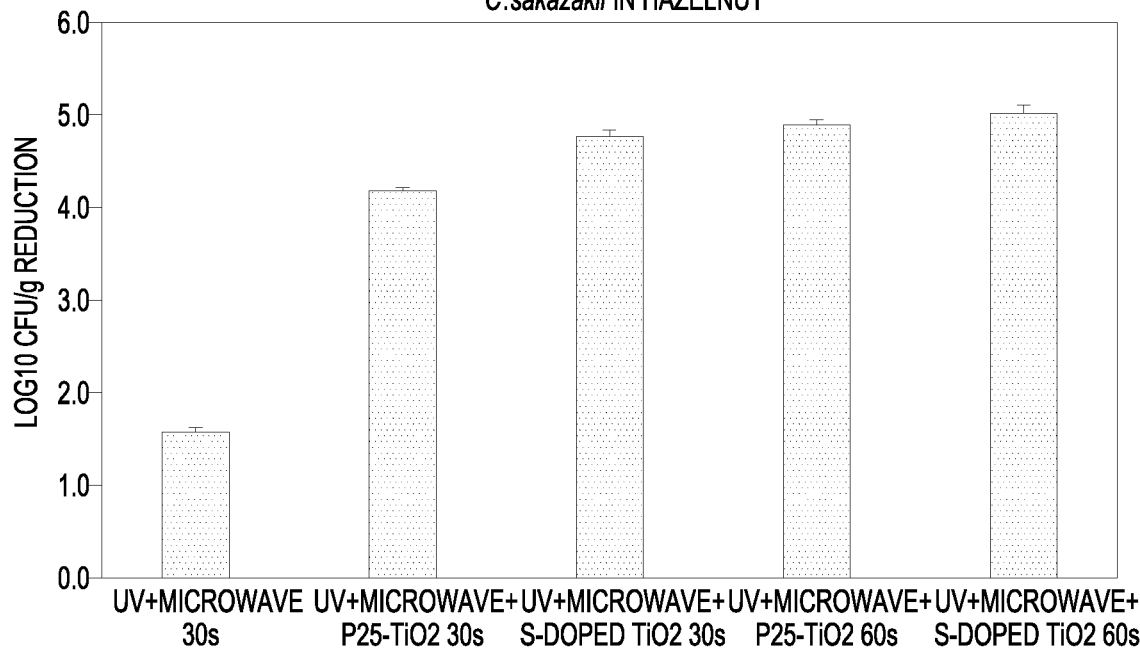
FIG. 4D shows the effect of catalytic microwave treatment on hazelnuts under different conditions.
Figure 4E:
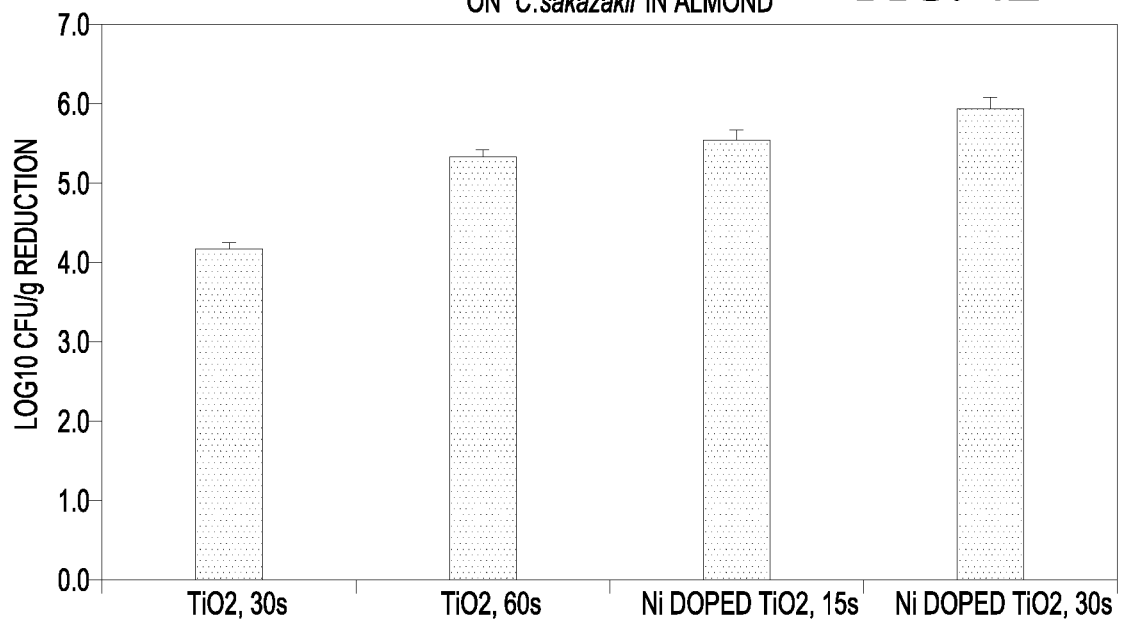
FIG. 4E shows the effect of catalytic microwave treatment on almonds under different conditions.

As shown in FIG. 4A, microwave treatment of wheat kernels inoculated with *C. sakizakii* results in 2.2 log CFU/g reduction for a 60 s microwave treatment such as that described with respect to FIG. 2. When TiO$_2$ photocatalyst was applied during microwave treatment, one additional log$_{10}$ reduction was achieved. The temperature profile during the treatments of microwave combined with TiO$_2$ is shown in FIG. 4B. FIG. 4C shows the effect of microwave treatment on hard red wheat kernels inoculated with *C. sakazakii, E. faecium*, and *B. cereus*, as well as a control sample (uninoculated) under different conditions. FIG. 4D shows the effect of catalytic microwave treatment on hazelnuts under different conditions. FIG. 4E shows the effect of catalytic microwave treatment on almonds under different conditions.

In summary, the cMAD data showed *C. sakazakii* and *E. faecium* were more effectively inactivated than *B. cereus* spores under the microwave treatment. Microwave treatment combined with high temperature led to a higher and more rapid microbial disinfection. The overall temperature of the food matrix was maintained below 60° C., thereby avoiding significant damage. It is believed that the temperature of bacteria was raised above 60° C., thereby inactivating them. Synergistic effects of the photocatalyst and microwave radiation resulted in an unexpectedly greater microbicidal effect.

Although this disclosure contains many specific embodiment details, these should not be construed as limitations on the scope of the subject matter or on the scope of what may be claimed, but rather as descriptions of features that may be specific to particular embodiments. Certain features that are described in this disclosure in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example embodiments do not define or constrain this disclosure. Other changes, substitutions, and alterations are also possible without departing from the spirit and scope of this disclosure.

What is claimed is:

1. A method of disinfecting particulate material, the method comprising:
    combining the particulate material with a photocatalyst to yield a mixture;
    irradiating the mixture for a length of time with pulses from a light source having broadband emission spectrum between 190 nm-1100 nm to yield an irradiated mixture, wherein irradiating the mixture inactivates microorganisms in the mixture to yield a disinfected mixture; and
    separating the photocatalyst from the disinfected mixture to yield the disinfected particulate matter,
    wherein the photocatalyst is disposed on a substrate to yield a photocatalytic substrate, the substrate comprises a polymer, a metal, or a metal oxide, and a weight ratio of the photocatalyst to the photocatalytic substrate is in a range of 1:1 to 1:100.

2. The method of claim 1, wherein the particulate mixture comprises a particulate food product or pharmaceutical product.

3. The method of claim 2, wherein the particulate mixture comprises grains, dried dairy products, flour, seasonings, seeds, or any combination thereof.

4. The method of claim 1, wherein the microorganisms comprise bacteria, fungi, viruses, protozoa, algae, spores associated therewith, or any combination thereof.

5. The method of claim 1, wherein the substrate is selected from the group consisting of polyethylene, quartz, silica, stainless steel, polystyrene, silicon carbide, aluminum oxide, and zirconium oxide.

6. The method of claim 1, wherein irradiating the mixture for a length of time comprises conveying the mixture under the pulsed ultraviolet radiation.

7. The method of claim 6, wherein the length of time is in a range of about 1 second to about 60 seconds.

8. The method of claim 1, wherein a frequency of the pulses is in a range of about 0.1 Hz to about 20 Hz.

9. The method of claim 1, wherein a duration of pulses is in a range of about 50 µs to about 70,000 µs.

10. The method of claim 1, wherein a voltage of the pulses is in a range of about 1000 V to about 3000 V.

11. The method of claim 1, wherein an energy of the pulses is up to about 2500 J/pulse.

12. The method of claim 1, wherein the photocatalyst comprises titanium dioxide.

13. A system for disinfecting particulate material, the system comprising:
    a pulsed light source having a broadband emission spectrum in a range between about 190 nm and about 1100 nm;
    a chamber defining a cavity optically coupled to the pulsed light source, wherein the chamber comprises a conveyor configured to accept the particulate material and arranged such that the pulses emitted by the pulsed light source irradiate the particulate material on the conveyor;
    a vibratory feeder configured to deliver the particulate material to the chamber;
    a volumetric feeder configured to adjust a feed rate of the particulate material to the conveyor;
    a humidifier;
    a fan; and
    one or more sensors.

14. The system of claim 13, further comprising a controller operatively coupled to the pulsed light source, the conveyor, the humidifier, the fan, and the one or more sensors.

15. The system of claim 13, wherein the one or more sensors comprises at least one of a temperature sensor, a humidity sensor, and an anemometer.

16. The system of claim 13, wherein a frequency of the pulses emitted by the pulsed light source is in a range of about 0.1 Hz to about 20 Hz.

17. The system of claim 13, wherein a duration of the pulses emitted by the pulsed light source is in a range of about 50 µs to about 70,000 µs.

18. The system of claim 13, wherein a voltage of the pulses emitted by the pulsed light source is in a range of about 1000 V to about 3000 V.

19. The system of claim 13, wherein an energy of the pulses emitted by the pulsed light source is up to about 2500 J/pulse.

20. The system of claim 13, wherein the conveyor comprises a photocatalyst and is configured to be irradiated with pulses emitted by the pulsed light source.

21. The system of claim 13, further comprising a surface coated with, including, or formed of a photocatalyst, wherein the surface is configured to reflect or concentrate pulses emitted by the pulsed light source to enhance disinfection of the particulate material on the conveyor.

22. The method of claim 1, wherein the substrate comprises magnetic particles.

23. The method of claim 22, wherein separating the photocatalyst from the disinfected mixture comprises application of a magnetic field to facilitate removal of the photocatalytic substrate from the disinfected particulate matter.

24. The method of claim 1, wherein the photocatalyst comprises $TiO_2$ and the substrate comprises $Al_2O_3$.

* * * * *